United States Patent
Thonnard

(12) 
(10) Patent No.: US 6,696,062 B1
(45) Date of Patent: Feb. 24, 2004

(54) **BASB006 POLYPEPTIDES FROM *NEISSERIA MENINGITIDIS* AND IMMUNOGENIC COMPOSITIONS THEREOF**

(75) Inventor: Joelle Thonnard, Gembloux (BE)

(73) Assignee: SmithKline Beecham Biologicals s.a., Rixensart (BE)

( * ) Notice: Subject to any disclaimer, the term of this patent is extended or adjusted under 35 U.S.C. 154(b) by 0 days.

(21) Appl. No.: 09/673,896

(22) PCT Filed: Apr. 20, 1999

(86) PCT No.: PCT/EP99/02766

§ 371 (c)(1),
(2), (4) Date: Dec. 18, 2000

(87) PCT Pub. No.: WO99/55873

PCT Pub. Date: Nov. 4, 1999

(30) Foreign Application Priority Data

Apr. 24, 1998 (GB) ............................................. 9808866

(51) Int. Cl.⁷ .............................................. A61K 39/02
(52) U.S. Cl. ................. 424/190.1; 424/192.1; 424/234.1; 424/250.1; 530/350
(58) Field of Search .......... 424/185.1, 190.1, 424/192.1, 234.1, 250.1; 530/300, 350

(56) References Cited

FOREIGN PATENT DOCUMENTS

| EP | 0 301 992 A | | 2/1989 |
|---|---|---|---|
| WO | WO 93 06861 | | 4/1993 |
| WO | 96/05858 | * | 2/1996 |
| WO | WO 96 33276 | | 10/1996 |
| WO | WO 97 26359 A | | 7/1997 |
| WO | 99/24578 | * | 5/1999 |

OTHER PUBLICATIONS

Protein Accession No. P44596 (Nov. 1, 1995), Fleishman et al Swiss Protein Database.

Fleischmann R.D., et al. "Whole Genome Random Sequencing and Assembly of Haemophilus Influenzae Rd" Science, 269:5223 pp. 496–512.

* cited by examiner

*Primary Examiner*—Patricia A. Duffy
(74) *Attorney, Agent, or Firm*—Jeffrey A. Sutton; Eric A. Meade

(57) ABSTRACT

Provided are BASB006 polypeptides from *Neisseria meningitidis*. Also provided are fusion proteins containing BASB006 polypeptides. The invention also relates to immunogenic compositions containing BASB006 polypeptides.

10 Claims, 19 Drawing Sheets

Figure 1A

Identity to SeqID No:1 is indicated by a dot, while a dash (-) indicates a nonexistent nucleotide.

```
                  *        20         *        40         *
Seqid1 : ATGAAAACAACCGACAAACGGACAACCGAAACACACCGCAAAGCCCCGAA :  50
Seqid3 : .................................................. :  50

60         *        80         *       100
Seqid1 : AACCGGTCGCATCCGCTTCTCGCCTGCTTACTTAGCCATATGCCTGTCGT : 100
Seqid3 : ......C........................................... : 100

*       120         *       140         *
Seqid1 : TCGGCATTCTTCCCCAAGCCTGGGCGGGACACACTTATTTCGGCATCAAC : 150
Seqid3 : .................................................. : 150

160         *       180         *       200
Seqid1 : TACCAATACTATCGCGACTTTGCCGAAAATAAAGGCAAGTTTGCAGTCGG : 200
Seqid3 : .................................................. : 200

*       220         *       240         *
Seqid1 : GGCGAAAGATATTGAGGTTTACAACAAAAAAGGGGAGTTGGTCGGCAAAT : 250
Seqid3 : .................................................. : 250

260         *       280         *       300
Seqid1 : CAATGACAAAAGCCCCGATGATTGATTTTCTGTGGTGTCGCGTAACGGC  : 300
Seqid3 : .................................................. : 300

*       320         *       340         *
Seqid1 : GTGGCGGCATTGGTGGGCGATCAATATATTGTGAGCGTGGCACATAACGG : 350
Seqid3 : .................................................. : 350
```

Figure 1B

```
              360         *         380         *         400
Seqid1 : CGGCTATAACAACGTTGATTTTGGTGCGGAGGGAAGCAATCCCGATCAGC :  400
Seqid3 : ...............................A.....A..........A. :  400

*         420         *         440         *
Seqid1 : ACCGTTTTTCTTATCAAATTGTGAAAAGAAATAATTATAAAGCAGGGACT :  450
Seqid3 : .T......A.....A...........C.G...................... :  450

460         *         480         *         500
Seqid1 : AACGGTCATCCTTATGGTGGCGATTATCATATGCCGCGTTTACATAAATT :  500
Seqid3 : ...A..C........................................... :  500

*         520         *         540         *
Seqid1 : TGTAACCGATGCAGAACCTGTTGAAATGACCAGTTATATGGATGGGCGGA :  550
Seqid3 : ...C..A........................................... :  550

560         *         580         *         600
Seqid1 : AATATATCGATCAAAATAATTACCCTGACCGTGTTCGTATTGGGGCAGGC :  600
Seqid3 : ................................................... :  600

*         620         *         640         *
Seqid1 : AGGCAATATTGGCGATCTGATGAAGATGAGCCCAATAACCGCGAAAGTTC :  650
Seqid3 : ................................................... :  650

660         *         680         *         700
Seqid1 : ATATCATATTGCAAGTGCGTATTCTTGGCTCGTTGGTGGCAATACCTTTG :  700
Seqid3 : ................................................... :  700

*         720         *         740         *
Seqid1 : CACAAAATGGATCAGGTGGTGGCACAGTCAACTTAGGTAGTGAAAAAATT :  750
Seqid3 : ................................................... :  750
```

Figure 1C

```
              760         *         780         *         800
Seqid1 : AAACATAGCCCATATGGTTTTTTACCAACAGGAGGCTCATTTGGCGACAG :  800
Seqid3 : ................................................. :  800

*         820         *         840         *
Seqid1 : TGGCTCACCAATGTTTATCTATGATGCCCAAAAGCAAAAGTGGTTAATTA :  850
Seqid3 : ................................................. :  850

860         *         880         *         900
Seqid1 : ATGGGGTATTGCAAACGGGCAACCCCTATATAGGAAAAAGCAATGGCTTC :  900
Seqid3 : ................................................. :  900

*         920         *         940         *
Seqid1 : CAGCTGGTTCGTAAAGATTGGTTCTATGATGAAATCTTTGCTGGAGATAC :  950
Seqid3 : ................................................. :  950

960         *         980         *        1000
Seqid1 : CCATTCAGTATTCTACGAACCACATCAAAATGGGAAATACACTTTTCACG : 1000
Seqid3 : ...................G....................T.....A.. : 1000

*        1020         *        1040         *
Seqid1 : ACAATAATAATGGCACAGGAAAAATCAATGCCAAACATGAACACAATTCT : 1050
Seqid3 : ..G.............................................. : 1050

1060        *        1080         *        1100
Seqid1 : CTGCCTAATAGATTAAAAACACGAACCGTTCAATTGTTTAATGTTTCTTT : 1100
Seqid3 : ................................................. : 1100

*        1120         *        1140         *
Seqid1 : ATCCGAGACAGCAAGAGAACCTGTTTATCATGCTGCAGGTGGTGTCAACA : 1150
Seqid3 : ................................................. : 1150
```

Figure 1D

```
              1160         *         1180         *         1200
Seqid1 : GTTATCGACCCAGACTGAATAATGGAGAAAATATTTCCTTTATTGACGAA : 1200
Seqid3 : .................................................. : 1200

*         1220         *         1240         *
Seqid1 : GGAAAAGGCGAATTGATACTTACCAGCAACATCAATCAAGGTGCTGGAGG : 1250
Seqid3 : .................................................. : 1250

1260         *         1280         *         1300
Seqid1 : ATTATATTTCCAAGGAGATTTTACGGTCTCGCCTGAAAATAACGAAACGT : 1300
Seqid3 : .................................................. : 1300

*         1320         *         1340         *
Seqid1 : GGCAAGGTGCGGGCGTTCATATCAGTGAAGACAGTACCGTTACTTGGAAA : 1350
Seqid3 : .................................................. : 1350

1360         *         1380         *         1400
Seqid1 : GTAAACGGCGTGGCAAACGACCGCCTGTCCAAAATCGGCAAAGGCACGCT : 1400
Seqid3 : .................................................. : 1400

*         1420         *         1440         *
Seqid1 : GCACGTTCAAGCCAAAGGGGAAAACCAAGGCTCGATCAGCGTGGGCGACG : 1450
Seqid3 : .................................................. : 1450

1460         *         1480         *         1500
Seqid1 : GTAAAGTTATTTTAGATCAACAAGCAGATGAAAATAATAAAAAACAAGCC : 1500
Seqid3 : ....C...C.....G.....G..G.....C..T..AGGC........... : 1500

*         1520         *         1540         *
Seqid1 : TTTAGTGAAATCGGCTTGGTCAGCGGCAGGGGTACGGTGCAACTGAATGC : 1550
Seqid3 : .................................................. : 1550
```

Figure 1E

```
                1560         *        1580         *        1600
Seqid1 : CGATAATCAGTTCAACCCCGACAAACTCTATTTCGGCTTTCGCGGCGGAC : 1600
Seqid3 : ..................................................  : 1600

*        1620         *        1640         *
Seqid1 : GTTTGGATTTGAACGGGCATTCGCTTTCGTTCCACCGTATTCAAAATACC : 1650
Seqid3 : .........A........................................ : 1650

1660         *        1680         *        1700
Seqid1 : GATGAAGGGGCGATGATTGTCAACCACAATCAAGACAAAGAATCCACCGT : 1700
Seqid3 : .................................................. : 1700

*        1720         *        1740         *
Seqid1 : TACCATTACAGGCAATAAAGATATTGCTACAACCGGCAATAACAACAGCT : 1750
Seqid3 : .................................................. : 1750

1760         *        1780         *        1800
Seqid1 : TGGATAGCAAAAAAGAAATTGCCTACAACGGTTGGTTTGGCGAGAAAGAT : 1800
Seqid3 : .................................................. : 1800

*        1820         *        1840         *
Seqid1 : ACGACCAAAACGAACGGGCGGCTCAACCTTGTTTACCAGCCCGCCGCAGA : 1850
Seqid3 : .................................................. : 1850

1860         *        1880         *        1900
Seqid1 : AGACCGCACCCTGCTGCTTTCCGGCGGAACAAATTTAAACGGTAACATCA : 1900
Seqid3 : ...........................................C...... : 1900

*        1920         *        1940         *
Seqid1 : CGCAAACAAACGGCAAACTGTTTTTCAGCGGCAGACCGACACCGCACGCC : 1950
Seqid3 : ..............................A................... : 1950
```

Figure 1F

```
              1960         *         1980          *        2000
Seqid1 : TACAATCATTTAGGAAGCGGGTGGTCAAAAATGGAAGGTATCCCACAAGG : 2000
Seqid3 : ..........AACGA.CAT.....GC...AA..G..C..T....GC.. : 2000

*        2020         *        2040          *
Seqid1 : AGAAATCGTGTGGGACAACGACTGGATCAACCGCACGTTTAAAGCGGAAA : 2050
Seqid3 : G................................A.............. : 2050

2060         *         2080          *        2100
Seqid1 : ATTTCCATATTCAGGGCGGGCAGGCGGTGATTTCCCGCAATGTTGCCAAA : 2100
Seqid3 : .C.....A..A.A.....A........G..................... : 2100

*        2120         *        2140          *
Seqid1 : GTGGAAGGCGATTGGCATTTGAGCAATCACGCCCAAGCAGTTTTTGGTGT : 2150
Seqid3 : ...A.............................................. : 2150

2160         *         2180          *        2200
Seqid1 : CGCACCGCATCAAAGCCACACAATCTGTACACGTTCGGACTGGACGGGTC : 2200
Seqid3 : .................................................. : 2200

*        2220         *        2240          *
Seqid1 : TGACAAATTGTGTCGAAAAAACCATTACCGACGATAAAGTGATTGCTTCA : 2250
Seqid3 : .................................................. : 2250

2260         *         2280          *        2300
Seqid1 : TTGACTAAGACCGACATCAGCGGCAATGTCAGCCTTGCCGATCACGCTCA : 2300
Seqid3 : ............................GAT................. : 2300

*        2320         *        2340          *
Seqid1 : TTTAAATCTCACAGGGCTTGCCACACTCAACGGCAATCTTAGTGCAAATG : 2350
Seqid3 : .................................................. : 2350
```

Figure 1G

```
              2360         *         2380         *         2400
Seqid1 : GCGATACACGTTATACAGTCAGCCACAACGCCACCCAAAACGGCGACCTT : 2400
Seqid3 : ...........................................A..... : 2400

*         2420         *         2440         *
Seqid1 : AGCCTCGTGGGCAATGCCCAAGCAACATTTAATCAAGCCACATTAAACGG : 2450
Seqid3 : .................................................. : 2450

2460         *         2480         *         2500
Seqid1 : CAACACATCGGCTTCGGGCAATGCTTCATTTAATCTAAGCAACAACGCCG : 2500
Seqid3 : ..............................G..C..... : 2500

*         2520         *         2540         *
Seqid1 : TACAAAACGGCAGTCTGACGCTTTCCGGCAACGCTAAGGCAAACGTAAGC : 2550
Seqid3 : .................................................. : 2550

2560         *         2580         *         2600
Seqid1 : CATTCCGCACTCAACGGTAATGTCTCCCTAGCCGATAAGGCAGTATTCCA : 2600
Seqid3 : .................................................. : 2600

*         2620         *         2640         *
Seqid1 : TTTTGAAAGCAGCCGCTTTACCGGACAAATCAGCGGCAGCAAGGATACGG : 2650
Seqid3 : ..............................G............ : 2650

2660         *         2680         *         2700
Seqid1 : CATTACACTTAAAAGACAGCGAATGGACGCTGCCGTCAGGCACGGAATTA : 2700
Seqid3 : .................................................. : 2700

*         2720         *         2740         *
Seqid1 : GGCAATTTAAACCTTGACAACGCCACCATTACACTCAATTCCGCCTATCG : 2750
Seqid3 : .................................................. : 2750
```

Figure 1H

```
              2760         *         2780         *         2800
Seqid1 : CCACGATGCGGCAGGGGCGCAAACCGGCAGTGCGACAGATGCGCCGCGC- : 2799
Seqid3 : .................................................C : 2800

*         2820         *         2840         *
Seqid1 : --------CGCCGTTCGCGCCGTTCCCTATTATCCGTTACACCTCCGGCT : 2841
Seqid3 : GCCGTTCG...............................G..AA.. : 2850

2860         *         2880         *         2900
Seqid1 : TCGGCAGAATCCCATTTCAACACGCTGACGGTAAACGGCAAATTGAACGG : 2891
Seqid3 : ....T......G.................................... : 2900

*         2920         *         2940         *
Seqid1 : TCAGGGAACATTCCGCTTTATGTCGGAACTCTTCGGCTACCGAAGCGACA : 2941
Seqid3 : ...............................C...... : 2950

2960         *         2980         *         3000
Seqid1 : AATTGAAGCTGGCGGAAAGTTCCGAAGGCACTTACACCTTGGCGGTCAAC : 2991
Seqid3 : .................................................. : 3000

*         3020         *         3040         *
Seqid1 : AATACCGGCAACGAACCCGTAAGCCTCGATCAATTGACGGTAGTGGAAGG : 3041
Seqid3 : ................T.C.....T..A................ : 3050

3060         *         3080         *         3100
Seqid1 : GAAAGACAACAAACCGCTGTCCGAAAACCTTAATTTCACCCTGCAAAACG : 3091
Seqid3 : A....................T.........T........ : 3100

*         3120         *         3140         *
Seqid1 : AACACGTCGATGCCGGCGCGTGGCGTTACCAACTCATCCGCAAAGACGGC : 3141
Seqid3 : .................................................. : 3150
```

Figure 1I

```
                 3160         *        3180         *        3200
Seqid1 : GAGTTCCGCCTGCATAATCCGGTCAAAGAACAAGAGCTTTCCGACAAACT : 3191
Seqid3 : ....................................................... : 3200

*        3220         *        3240         *
Seqid1 : CGGCAAGGCAGAAGCCAAAAAACAGGCGGGAAAAGACAACGCGCAAAGCC : 3241
Seqid3 : ..............................A.................. : 3250

3260         *        3280         *        3300
Seqid1 : TTGACGCGCTGATTGCGGCCGGGCGCGATGCCGTCGAAAAGACAGAAAGC : 3291
Seqid3 : ....................................................... : 3300

*        3320         *        3340         *
Seqid1 : GTTGCCGAACCGGCCCGGCAGGCAGGCGGGGAAAATGTCGGCATTATGCA : 3341
Seqid3 : ....................................................... : 3350

3360         *        3380         *        3400
Seqid1 : GGCGGAGGAAGAGAAAAAACGGGTGCAGGCGGATAAAGACACCGCCTTGG : 3391
Seqid3 : ....................................................... : 3400

*        3420         *        3440         *
Seqid1 : CGAAACAGCGCGAAGGGAAAACCCGGCCGGCTACCACCGCCTTCCCCCGC : 3441
Seqid3 : .............C.G................................. : 3450

3460         *        3480         *        3500
Seqid1 : GCCCGCCGCGCCCGCCGGGATTTGCCGCAACCGCAGCCCCAACCGCAACC : 3491
Seqid3 : ........................T..A..........G.. : 3500

*        3520         *        3540         *
Seqid1 : CCAACCGCAGCGCGACCTGATCAGCCGTTATGCCAATAGCGGTTTGAGTG : 3541
Seqid3 : ....................................................... : 3550
```

Figure 1J

```
                  3560         *          3580         *          3600
Seqid1 : AATTTTCCGCCACGCTCAACAGCGTTTTCGCCGTACAGGACGAATTAGAC : 3591
Seqid3 : ................................................ : 3600

*          3620         *          3640         *
Seqid1 : CGCGTATTTGCCGAAGACCGCCGCAACGCCGTTTGGACAAGCGGCATCCG : 3641
Seqid3 : ..............A................................. : 3650

3660         *          3680         *          3700
Seqid1 : GGACACCAAACACTACCGTTCGCAAGATTTCCGCGCCTACCGCCAACAAA : 3691
Seqid3 : ................................................ : 3700

*          3720         *          3740         *
Seqid1 : CCGACCTGCGCCAAATCGGTATGCAGAAAAACCTCGGCAGCGGGCGCGTC : 3741
Seqid3 : ................................................ : 3750

3760         *          3780         *          3800
Seqid1 : GGCATCCTGTTTTCGCACAACCGGACCGAAAACACCTTCGACGACGGCAT : 3791
Seqid3 : ................................................ : 3800

*          3820         *          3840         *
Seqid1 : CGGCAACTCGGCACGGCTTGCCCACGGCGCCGTTTTCGGGCAATACGGCA : 3841
Seqid3 : ................................................ : 3850

3860         *          3880         *          3900
Seqid1 : TCGGCAGGTTCGACATCGGCATCAGCACGGGCGCGGGTTTTAGCAGCGGC : 3891
Seqid3 : ...A......T...........G.......................... : 3900

*          3920         *          3940         *
Seqid1 : AGTCTTTCAGACGACATCGGAAGCAAAATCCGCCGCCGCGTGCTGCATTA : 3941
Seqid3 : ...C........G.....G.............................. : 3950
```

Figure 1K

```
               3960         *         3980         *         4000
Seqid1 : CGGCATTCAGGCACGATACCGCGCCGGTTTCGGCGGATTCGGCATCGAAC : 3991
Seqid3 : ....................................................... : 4000

*         4020         *         4040         *
Seqid1 : CGCACATCGGCGCAACGCGCTATTTCGTCCAAAAAGCGGATTACCGCTAC : 4041
Seqid3 : ....................................................... : 4050

4060         *         4080         *         4100
Seqid1 : GAAAACGTCAATATCGCCACCCCCGGCCTTGCGTTCAACCGCTACCGCGC : 4091
Seqid3 : ............................A..................... : 4100

*         4120         *         4140         *
Seqid1 : GGGCATTAAGGCAGATTATTCATTCAAACCGGCGCAACACATTTCCATCA : 4141
Seqid3 : ....................................................... : 4150

4160         *         4180         *         4200
Seqid1 : CGCCTTATTTGAGCCTGTCCTATACCGATGCCGCTTCGGGCAAAGTCCGA : 4191
Seqid3 : ....................................................... : 4200

*         4220         *         4240         *
Seqid1 : ACGCGCGTCAATACCGCCGTATTGGCTCAGGATTTCGGCAAAACCCGCAG : 4241
Seqid3 : ...A................................................ : 4250

4260         *         4280         *         4300
Seqid1 : TGCGGAATGGGGCGTAAACGCCGAAATCAAAGGTTTCACGCTGTCCCTCC : 4291
Seqid3 : ..............................C..................... : 4300

*         4320         *         4340         *
Seqid1 : ACGCTGCCGCCGCCAAAGGCCCGCAACTGGAAGCGCAACACAGCGCGGGC : 4341
Seqid3 : ....................................................... : 4350
```

Figure 1L

```
              4360           *
Seqid1 : ATCAAATTAGGCTACCGCTGGTAA : 4365
Seqid3 : ....................... : 4374
```

Figure 2A

Identity to SeqID No:2 is indicated by a dot, while a dash (-) indicates a nonexistent amino acid.

```
                  *        20         *        40         *
Seqid2 : MKTTDKRTTETHRKAPKTGRIRFSPAYLAICLSFGILPQAWAGHTYFGIN :  50
Seqid4 : .................................................. :  50

60        *        80         *       100
Seqid2 : YQYYRDFAENKGKFAVGAKDIEVYNKKGELVGKSMTKAPMIDFSVVSRNG : 100
Seqid4 : .................................................. : 100

*       120         *       140         *
Seqid2 : VAALVGDQYIVSVAHNGGYNNVDFGAEGSNPDQHRFSYQIVKRNNYKAGT : 150
Seqid4 : ........................R.......T.K............ : 150

160         *       180         *       200
Seqid2 : NGHPYGGDYHMPRLHKFVTDAEPVEMTSYMDGRKYIDQNNYPDRVRIGAG : 200
Seqid4 : K................................................ : 200

*       220         *       240         *
Seqid2 : RQYWRSDEDEPNNRESSYHIASAYSWLVGGNTFAQNGSGGGTVNLGSEKI : 250
Seqid4 : .................................................. : 250

260         *       280         *       300
Seqid2 : KHSPYGFLPTGGSFGDSGSPMFIYDAQKQKWLINGVLQTGNPYIGKSNGF : 300
Seqid4 : .................................................. : 300

*       320         *       340         *
Seqid2 : QLVRKDWFYDEIFAGDTHSVFYEPHQNGKYTFHDNNNGTGKINAKHEHNS : 350
Seqid4 : ........................R.....S.N.D............. : 350
```

Figure 2B

```
                360          *          380          *          400
Seqid2 : LPNRLKTRTVQLFNVSLSETAREPVYHAAGGVNSYRPRLNNGENISFIDE :  400
Seqid4 : .................................................. :  400

*          420          *          440          *
Seqid2 : GKGELILTSNINQGAGGLYFQGDFTVSPENNETWQGAGVHISEDSTVTWK :  450
Seqid4 : .................................................. :  450

460          *          480          *          500
Seqid2 : VNGVANDRLSKIGKGTLHVQAKGENQGSISVGDGKVILDQQADENNKKQA :  500
Seqid4 : ...............................T......DKG....     :  500

*          520          *          540          *
Seqid2 : FSEIGLVSGRGTVQLNADNQFNPDKLYFGFRGGRLDLNGHSLSFHRIQNT :  550
Seqid4 : .................................................. :  550

560          *          580          *          600
Seqid2 : DEGAMIVNHNQDKESTVTITGNKDIATTGNNNSLDSKKEIAYNGWFGEKD :  600
Seqid4 : .................................................. :  600

*          620          *          640          *
Seqid2 : TTKTNGRLNLVYQPAAEDRTLLLSGGTNLNGNITQTNGKLFFSGRPTPHA :  650
Seqid4 : .................................................. :  650

660          *          680          *          700
Seqid2 : YNHLGSGWSKMEGIPQGEIVWDNDWINRTFKAENFHIQGGQAVISRNVAK :  700
Seqid4 : ....NDH..QK....R...............Q.K....V......     :  700

*          720          *          740          *
Seqid2 : VEGDWHLSNHAQAVFGVAPHQSHTICTRSDWTGLTNCVEKTITDDKVIAS :  750
Seqid4 : .K................................................ :  750
```

Figure 2C

```
              760         *         780         *         800
Seqid2 : LTKTDISGNVSLADHAHLNLTGLATLNGNLSANGDTRYTVSHNATQNGDL :  800
Seqid4 : .........D.............................N.         :  800

*         820         *         840         *
Seqid2 : SLVGNAQATFNQATLNGNTSASGNASFNLSNNAVQNGSLTLSGNAKANVS :  850
Seqid4 : ..............................DH.................:  850

860         *         880         *         900
Seqid2 : HSALNGNVSLADKAVFHFESSRFTGQISGSKDTALHLKDSEWTLPSGTEL :  900
Seqid4 : ................................G................:  900

*         920         *         940         *
Seqid2 : GNLNLDNATITLNSAYRHDAAGAQTGSATDAPR---RRSRRSLLSVTPPA :  947
Seqid4 : ................................RRS..........T   :  950

960         *         980         *        1000
Seqid2 : SAESHFNTLTVNGKLNGQGTFRFMSELFGYRSDKLKLAESSEGTYTLAVN :  997
Seqid4 : .V..R.............................................: 1000

*        1020         *        1040         *
Seqid2 : NTGNEPVSLDQLTVVEGKDNKPLSENLNFTLQNEHVDAGAWRYQLIRKDG : 1047
Seqid4 : .....A..E...........F............................: 1050

1060         *        1080         *        1100
Seqid2 : EFRLHNPVKEQELSDKLGKAEAKKQAGKDNAQSLDALIAAGRDAVEKTES : 1097
Seqid4 : ..............................E..................: 1100

*        1120         *        1140         *
Seqid2 : VAEPARQAGGENVGIMQAEEEKKRVQADKDTALAKQREGKTRPATTAFPR : 1147
Seqid4 : ..............................................AE........: 1150
```

Figure 2D

```
              1160           *          1180           *          1200
Seqid2 : ARRARRDLPQPQPQPQPQPQRDLISRYANSGLSEFSATLNSVFAVQDELD : 1197
Seqid4 : .........L...................................... :  1200

*          1220           *          1240           *
Seqid2 : RVFAEDRRNAVWTSGIRDTKHYRSQDFRAYRQQTDLRQIGMQKNLGSGRV : 1247
Seqid4 : .....E........................................... :  1250

1260           *          1280           *          1300
Seqid2 : GILFSHNRTENTFDDGIGNSARLAHGAVFGQYGIGRFDIGISTGAGFSSG : 1297
Seqid4 : ...........................D..Y....A............ :  1300

*          1320           *          1340           *
Seqid2 : SLSDDIGSKIRRRVLHYGIQARYRAGFGGFGIEPHIGATRYFVQKADYRY : 1347
Seqid4 : ....G..G......................................... :  1350

1360           *          1380           *          1400
Seqid2 : ENVNIATPGLAFNRYRAGIKADYSFKPAQHISITPYLSLSYTDAASGKVR : 1397
Seqid4 : ................................................. :  1400

*          1420           *          1440           *
Seqid2 : TRVNTAVLAQDFGKTRSAEWGVNAEIKGFTLSLHAAAAKGPQLEAQHSAG : 1447
Seqid4 : ................................................. :  1450

Seqid2 : IKLGYRW : 1454
Seqid4 : ....... :  1457
```

Anti-BASB006 antibodies in human convalescent sera (part B) and in immunized mice (part A).

BASB006 POLYPEPTIDES FROM *NEISSERIA MENINGITIDIS* AND IMMUNOGENIC COMPOSITIONS THEREOF

This application claims the priority of GB Application No. 9808866.9, filed Apr. 24, 1998.

FIELD OF THE INVENTION

This invention relates to polynucleotides, (herein referred to as "BASB006 polynucleotide(s)"), polypeptides encoded by them (referred to herein as "BASB006" or "BASB006 polypeptide(s)"), recombinant materials and methods for their production. In another aspect, the invention relates to methods for using such polypeptides and polynucleotides, including vaccines against bacterial infections. In a further aspect, the invention relates to diagnostic assays for detecting infection of certain pathogens.

BACKGROUND OF THE INVENTION

*Neisseria meningitidis* (meningococcus) is a Gram negative bacterium frequently isolated from the human upper respiratory tract. It occasionally causes invasive bacterial diseases such as bacteremia and meningitis. The incidence of meningococcal disease shows geographical seasonal and annual differences (Schwartz, B., Moore, P. S., Broome, C. V.; Clin. Microbiol. Rev. 2 (Supplement), S18–S24, 1989). Most disease in temperate countries is due to strains of serogroup B and varies in incidence from 1–10/100,000/year total population sometimes reaching higher values (Kaczmarski, E. B. (1997), Commun. Dis. Rep. Rev. 7: R55–9, 1995; Scholten, R. J. P. M., Bijlmer, H. A., Poolman, J. T. et al. Clin. Infect. Dis. 16: 237–246, 1993; Cruz, C., Pavez, G., Aguilar, E., et al. Epidemiol. Infect. 105: 119–126, 1990).

Epidemics dominated by serogroup. A meningococci, mostly in central Africa, are encountered, sometimes reaching levels up to 1000/100.000/year (Schwartz, B., Moore. P. S., Broome, C. V. Clin. Microbiol. Rev. 2 (Supplement), S18–S24, 1989). Nearly all cases as a whole of meningococcal disease are caused by serogroup A, B, C, W-135 and Y meningococci and a tetravalent A, C, W-135, Y polysaccharide vaccine is available (Armand, J., Arminjon, F., Mynard, M. C., Lafaix, C., J. Biol. Stand. 10: 335–339, 1982).

The polysaccharide vaccines are currently being improved by way of chemical conjugating them to carrier proteins (Lieberman, J. M., Chiu, S. S., Wong, V. K., et al. JAMA 275: 1499–1503, 1996).

A serogroup B vaccine is not available, since the B capsular polysaccharide was found to be nonimmunogenic, most likely because it shares structural similarity to host components (Wyle. F. A., Artenstein. M. S., Brandt, M. L. et al. J. Infect. Dis. 126: 514–522. 1972; Finne. J. M., Leinonen, M., Mäkelä, P. M. Lancet ii.: 355–357, 1983).

For many years efforts have been initiated and carried out to develop meningococcal outer membrane based vaccines (de Moraes, J. C., Perkins, B., Camargo, M. C. et al. Lancet 340: 1074–1078, 1992; Bjune, G., Hoiby, E. A. Gronnesby, J. K. et al. 338: 1093–1096, 1991). Such vaccines have demonstrated efficcacies from 57%–85% in older children (>4 years) and adolescents.

Many bacterial outer membrane components are present in these vaccines, such as PorA, PorB, Rmp, Opc, Opa, FrpB and the contribution of these components to the observed protection still needs further definition. Other bacterial outer membrane components have been defined by using animal or human antibodies to be potentially relevant to the induction of protective immunity, such as TbpB and NspA (Martin, D., Cadieux, N., Hamel, J., Brodeux, B. R., J. Exp. Med. 185: 1173–1183, 1997; Lissolo, L., Maitre-Wilmotte, C., Dumas, p. et al., Inf. Immnun. 63: 884–890, 1995). The mechanisms of protective immunity will involve antibody mediated bactericidal activity and opsonophagocytosis.

A bacteremia animal model has been used to combine all antibody mediated mechanisms (Saukkonen, K., Leinonen, M., Abdillahi, H. Poolman, J. T. Vaccine 7: 325–328, 1989). It is generally accepted that the late complement component mediated bactericidal mechanism is crucial for immunity against meningococcal disease (Ross. S. C., Rosenthal P. J., Berberic, H. M., Densen, P. J. Infect. Dis. 155: 1266–1275. 1987).

The frequency of *Neisseria meningitidis* infections has risen dramatically in the past few decades. This has been attributed to the emergence of multiply antibiotic resistant strains and an increasing population of people with weakened immune systems. It is no longer uncommon to isolate *Neisseria meningitidis* strains that are resistant to some or all of the standard antibiotics. This phenomenon has created an unmet medical need and demand for new anti-microbial agents, vaccines, drug screening methods, and diagnostic tests for this organism.

SUMMARY OF THE INVENTION

The present invention relates to BASB006, in particular BASB006 polypeptides and BASB006 polynucleotides, recombinant materials and methods for their production. In another aspect, the invention relates to methods for using such polypeptides and polynucleotides, including prevention and treatment of microbial diseases, amongst others. In a further aspect, the invention relates to diagnostic assays for detecting diseases associated with microbial infections and conditions associated with such infections, such as assays for detecting expression or activity of BASB006 polynucleotides or polypeptides.

Various changes and modifications within the spirit and scope of the disclosed invention will become readily apparent to those skilled in the art from reading the following descriptions and from reading the other parts of the present disclosure.

FIGS. 1A–1L show consecutive segments of sequence alignments for two BASB006-encoding polynucleotides.

FIGS. 2A–2D show consecutive segments of sequence alignments for two BASB006 polypeptides.

DESCRIPTION OF THE INVENTION

Figure 3:
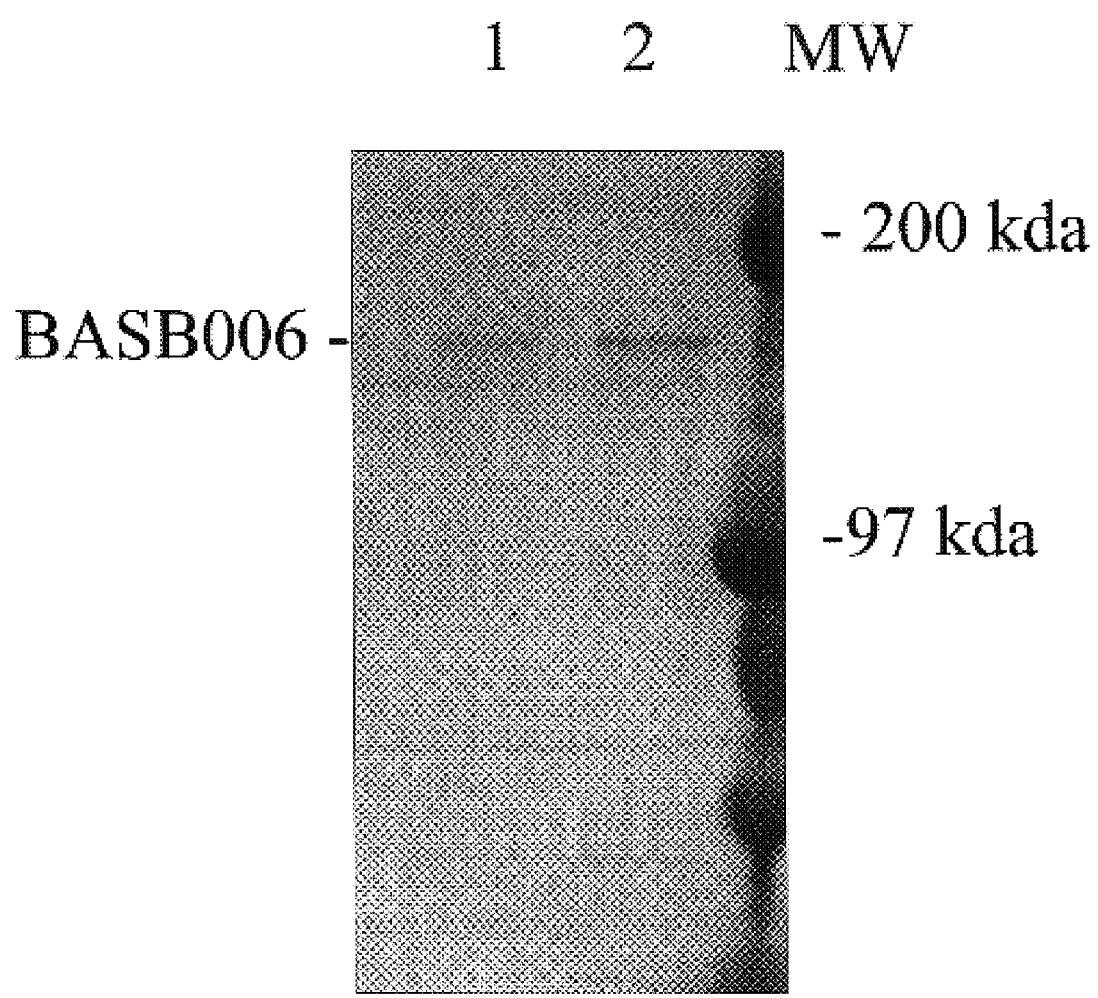
FIG. 3 shows a Coomassie stain SDS-PAGE gel analysis of purified BASB006 protein.

The invention relates to BASB006 polypeptides and polynucleotides as described in greater detail below. In particular, the invention relates to polypeptides and polynucleotides of BASB006 of *Neisseria meningitidis*, which is related by amino acid sequence homology to *H. influenzae* Hap polypeptide. The invention relates especially to BASB006 having the nucleotide and amino acid sequences set out in SEQ ID NO:13 and SEQ ID NO:2,4 respectively. It is understood that sequences recited in the Sequence Listing below as "DNA" represent an exemplification of one embodiment of the invention. since those of ordinary skill will recognize that such sequences can be usefully employed in polynucleotides in general, including ribopolynucleotides.

Polypeptides

In one aspect of the invention there are provided polypeptides of *Neisseria meningitidis* referred to herein as "BASB006" and "BASB006 polypeptides" as well as biologically, diagnostically, prophylactically, clinically or therapeutically useful variants thereof, and compositions comprising the same.

The present invention further provides for:

(a) an isolated polypeptide which comprises an amino acid sequence which has at least 85% identity, more preferably at least 90% identity, yet more preferably at least 95% identity, most preferably at least 97–99% or exact identity, to that of SEQ ID NO:2, 4;

(b) a polypeptide encoded by an isolated polynucleotide comprising a polynucleotide sequence which has at least 85% identity, more preferably at least 90% identity, yet more preferably at least 95% identity, even more preferably at least 97–99% or exact identity to SEQ ID NO:1, 3 over the entire length of SEQ ID NO:1, 3 respectively; or (c) a polypeptide encoded by an isolated polynucleotide comprising a polynucleotide sequence encoding a polypeptide which has at least 85% identity, more preferably at least 90% identity, yet more preferably at least 95% identity, even more preferably at least 97–99% or exact identity, to the amino acid sequence of SEQ ID NO:2. 4;

The BASB006 polypeptides provided in SEQ ID NO:2,4 are the BASB006 polypeptides from *Neisseria meningitidis* strains American Type Culture Collection 13090 (herein "ATCC 13090") and H44/76.

The invention also provides an immunogenic fragment of a BASB006 polypeptide, that is, a contiguous portion of the BASB006 polypeptide which has the same or substantially the same immunogenic activity as the polypeptide comprising the amino acid sequence of SEQ ID NO:2,4. That is to say, the fragment (if necessary when coupled to a carrier) is capable of raising an immune response which recognises the BASB006 polypeptide Such an immunogenic fragment may include, for example, the BASB006 polypeptide lacking an N-terminal leader sequence, and/or a transmembrane domain and/or a C-terminal anchor domain. In a preferred aspect the immunogenic fragment of BASB006 according to the invention comprises substantially all of the extracellular domain of a polypeptide which has at least 85% identity, more preferably at least 90% identity, yet more preferably at least 95% identity, most preferably at least 97–99% identity, to that of SEQ ID NO:2,4 over the entire length of SEQ ID NO:2

A fragment is a polypeptide having an amino acid sequence that is entirely the same as part but not all of any amino acid sequence of any polypeptide of the invention. As with BASB006 polypeptides, fragments may be "freestanding" or comprised within a larger polypeptide of which they form a part or region, most preferably- as a single continuous region in a single larger polypeptide.

Preferred fragments include, for example, truncation polypeptides having a portion of an amino acid sequence of SEQ ID NO:2,4 or of variants thereof, such as a continuous series of residues that includes an amino- and/or carboxyl-terminal amino acid sequence.

Degradation forms of the polypeptides of the invention produced by or in a host cell, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:2,4, or an isolated polypeptide comprising an amino acid sequence having at least 15, 20, 30, 40, 50 or 100 contiguous amino acids truncated or deleted from the amino acid sequence of SEQ ID NO:2,4.

Fragments of the polypeptides of the invention may be employed for producing the corresponding full-length polypeptide by peptide synthesis; therefore, these fragments may be employed as intermediates for producing the full-length polypeptides of the invention.

Particularly preferred are variants in which several, 5-10, 1-5, 1-3, 1-2 or 1 amino acids are substituted, deleted, or added in any combination.

The polypeptides, or immunogenic fragments, of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, Ig, IgA, IgE). Preferred as an immunoglobulin is the constant part of the heavy chain of human IgG, particularly IgG 1, where fusion takes place at the hinge region. In a particular embodiment, the Fc part can be removed simply by incorporation of a cleavage sequence which can be cleaved with blood clotting factor Xa.

Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. The fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenzae* and the non-structural protein from influenzae virus, NS1 (hemagglutinin). Another fusion partner is the protein known as LytA. Preferably the C terminal portion of the molecule is used. LytA is derived from *Streptococcus pneumoniae* which synthesize an N-acetyl-L-alanine amidase, amidase LytA, (coded by the lytA gene {Gene, 43 (1986) page 265–272}) an autolysin that specifically degrades certain bonds in the peptidoglycan backbone. The C-terminal domain of the LytA protein is responsible for the affinity to the choline or to some choline analogues such as DEAE. This property has been exploited for the development of *E. coli* C-LytA expressing plasmids useful for expression of fusion proteins. Purification of hybrid proteins containing the C-LytA fragment at its amino terminus has been described {Biotechnology: 10, (1992) page 795–798}. It is possible to use the repeat portion of the LytA molecule found in the C terminal end starting at residue 178, for example residues 188–305.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

It is most preferred that a polypeptide of the invention is derived from *Neisseria meningitidis*, however, it may preferably be obtained from other organisms of the same taxonomic genus. A polypeptide of the invention may also be obtained, for example, from organisms of the same taxonomic family or order.

Polynucleotides

It is an object of the invention to provide polynucleotides that encode BASB006 polypeptides, particularly polynucleotides that encode the polypeptide herein designated BASB006.

In a particularly preferred embodiment of the invention the polynucleotide comprises a region encoding BASB006 polypeptides comprising a sequence set out in SEQ ID NO:1,3 which includes a full length gene, or a variant thereof.

The BASB006 polynucleotides provided in SEQ ID NO:1,3 are the BASB006 polynucleotides from *Neisseria meningitidis* strains ATCC 13090 and H44/76.

As a further aspect of the invention there are provided isolated nucleic acid molecules encoding and/or expressing BASB006 polypeptides and polynucleotides, particularly *Neisseria meningitidis* BASB006 polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a BASB006 polypeptide having a deduced amino acid sequence of SEQ ID NO:2,4 and polynucleotides closely related thereto and variants thereof.

In another particularly preferred embodiment of the invention there is a BASB006 polypeptide from *Neisseria meningitidis* comprising or consisting of an amino acid sequence of SEQ ID NO:2,4 or a variant thereof.

Using the information provided herein, such as a polynucleotide sequence set out in SEQ ID NO:1, 3 a polynucleotide of the invention encoding BASB006 polypeptide may be obtained using standard cloning and screening methods, such as those for cloning and sequencing chromosomal DNA fragments from bacteria using *Neisseria meningitidis* cells as starting material, followed by obtaining a full length clone. For example, to obtain a polynucleotide sequence of the invention, such as a polynucleotide sequence given in SEQ ID NO:1,3, typically a library of clones of chromosomal DNA of *Neisseria meningitidis* in *E.coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed for example, using denatured double stranded DNA prepared from a plasmid clone. Suitable techniques are described by Maniatis. T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in SEQ ID NO:1,3 was discovered in a DNA library derived from *Neisseria meningitidis*.

Moreover, each DNA sequence set out in SEQ ID NO:1,3 contains an open reading frame encoding a protein having about the number of amino acid residues set forth in SEQ ID NO:2, 4 with a deduced molecular weight that can be calculated using amino acid residue molecular weight values well known to those skilled in the art.

The polynucleotide of SEQ ID NO:1, between the start codon at nucleotide number 1 and the stop codon which begins at nucleotide number 4363 of SEQ ID NO:1, encodes the polypeptide of SEQ ID NO:2.

The polynucleotide of SEQ ID NO:3, between the start codon at nucleotide number 1 and the stop codon which begins at nucleotide number 4372 of SEQ ID NO:3, encodes the polypeptide of SEQ ID NO:4.

In a further aspect, the present invention provides for an isolated polynucleotide comprising or consisting of:

(a) a polynucleotide sequence which has at least 85% identity, more preferably at least 90% identity, yet more preferably at least 95% identity, even more preferably at least 97–99% or exact identity to SEQ ID NO:1,3 over the entire length of SEQ ID NO:1,3 respectively; or (b) a polynucleotide sequence encoding a polypeptide which has at least 85% identity, more preferably at least 90% identity, yet more preferably at least 95% identity, even more preferably at least 97–99% or 100% exact, to the amino acid sequence of SEQ ID NO:2, 4 over the entire length of SEQ ID NO:2, 4 respectively.

A polynucleotide encoding a polypeptide of the present invention, including homologs and orthologs from species other than *Neisseria meningitidis*, may be obtained by a process which comprises the steps of screening an appropriate library under stringent hybridization conditions (for example, using a temperature in the range of 45–65° C. and an SDS concentration from 0.1–1%) with a labeled or detectable probe consisting of or comprising the sequence of SEQ ID NO:1, 3 or a fragment thereof; and isolating a full-length gene and/or genomic clones containing said polynucleotide sequence.

The invention provides a polynucleotide sequence identical over its entire length to a coding sequence (open reading frame) in SEQ ID NO:1, 3. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or preproprotein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

The nucleotide sequence encoding BASB006 polypeptide of SEQ ID NO:2, 4 may be identical to the polypeptide encoding sequence contained in nucleotides 1 to 4362 of SEQ ID NO:1, or the polypeptide encoding sequence contained in nucleotides 1 to 4371 of SEQ ID NO:3, respectively. Alternatively it may be a sequence, which as a result of the redundancy (degeneracy) of the genetic code, also encodes the polypeptide of SEQ ID NO:2, 4.

The term "polynucleotide encoding a polypeptide" as used herein encompasses polynucleotides that include a sequence encoding a polypeptide of the invention, particularly a bacterial polypeptide and more particularly a polypeptide of the *Neisseria meningitidis* BASB006 having an amino acid sequence set out in SEQ ID NO:2, 4. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of SEQ ID NO:2, 4. Fragments of polynucleotides of the invention may be used, for example, to synthesize full-length polynucleotides of the invention.

Further particularly preferred embodiments are polynucleotides encoding BASB006 variants, that have the amino acid sequence of BASB006 polypeptide of SEQ ID NO:2, 4 in which several, a few, 5 to 10, 1 to 5, 1 to 3, 2, 1 or no amino acid residues are substituted. modified, deleted and/or added, in any combination. Especially preferred among these are silent substitutions, additions and deletions, that do not alter the properties and activities of BASB006 polypeptide.

Further preferred embodiments of the invention are polynucleotides that are at least 85% identical over their entire length to a polynucleotide encoding BASB006 polypeptide having an amino acid sequence set out in SEQ ID NO:2, 4, and polynucleotides that are complementary to such polynucleotides. In this regard, polynucleotides at least 90% identical over their entire length to the same are particularly preferred, and among these particularly preferred polynucleotides, those with at least 95% are especially preferred.

Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of SEQ ID NO:1,3.

In accordance with certain preferred embodiments of this invention there are provided polynucleotides that hybridize, particularly under stringent conditions, to BASB006 polynucleotide sequences, such as those polynucleotides in SEQ ID NO:1, 3.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:1, 3 under stringent hybridization conditions with a probe having the sequence of said polynucleotide sequence set forth in SEQ ID NO:1, 3 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA. cDNA and genomic DNA to isolate full-length cDNAs and genomic clones encoding BASB006 and to isolate cDNA and genomic clones of other genes that have a high identity, particularly high sequence identity, to the BASB006 gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a BASB006 gene may be isolated by screening using a DNA sequence provided in SEQ ID NO:1, 3 to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al., *PNAS USA* 85: 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of SEQ ID NOS: 1–4 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In accordance with an aspect of the invention, there is provided the use of a polynucleotide of the invention for therapeutic or prophylactic purposes, in particular genetic immunization.

The use of a polynucleotide of the invention in genetic immunization will preferably employ a suitable delivery method such as direct injection of plasmid DNA into muscles (Wolffet cl., *Hum Mol Genet* (1992) 1: 363, Manthorpe et al., *Hum. Gene Ther.* (1983) 4: 419), delivery of DNA complexed with specific protein carriers (Wu et al., *J Biol Chem.* (1989) 264: 16985), coprecipitation of DNA with calcium phosphate (Benvenisty & Reshef, *PNAS USA,* (1986) 83: 9551), encapsulation of DNA in various forms of liposomes (Kaneda et al., *Science* (1989) 243: 375), particle bombardment (Tang et al., *Nature* (1992) 356:152, Eisenbraun et al., *DNA Cell Biol* (1993) 12: 791) and in vivo infection using cloned retroviral vectors (Seeger et al., *PNAS USA* (1984) 81: 5849).

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis. et al., *BASIC METHODS IN MOLECULAR BIOLOGY*, (1986) and Sambrook. et al., *MOLECULAR CLONING: A LABORATORY MANUAL*. 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as cells of streptococci, staphylococci, enterococci, *E. coli*, streptomyces, cyanobacteria, *Bacillus subtilis, Moraxella catarrhalis, Haemophilus influenzae* and *Neisseria meningitidis*; fungal cells, such as cells of a yeast, Kluyveromyces, Saccharomyces, a basidiomycete, *Candida albicans* and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses, retroviruses, and alphaviruses and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g; vaccinia. fowlpox, canarypox), alphaviruses (Sindbis virus, Semliki Forest Virus. Venezuelian Equine Encephalitis Virus), adenoviruses, adeno-associated virus, picornaviruses (poliovirus, rhinovirus), herpesviruses (varicella zoster virus, etc), Listeria, Salmonella , Shigella, Neisseria, BCG. These viruses and bacteria can be virulent, or attenuated in various ways in order to obtain live vaccines. Such live vaccines also form part of the invention.

Diagnostic, Prognostic, Serotyping and Mutation Assays

This invention is also related to the use of BASB006 polynucleotides and polypeptides of the invention for use as diagnostic reagents. Detection of BASB006 polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the BASB006 gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled BASB006 polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science*, 230: 1242 (1985). Sequence changes at specific locations also may be revealed by nuclease protection assays, such as RNase, V1 and S1 protection assay or a chemical cleavage method. See, for example, Cotton et al., *Proc. Natl. Acad. Sci., USA*, 85: 4397–4401 (1985).

In another embodiment, an array of oligonucleotides probes comprising BASB006 nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., *Science,* 274: 610 (1996)).

Thus in another aspect, the present invention relates to a diagnostic kit which comprises:

(a) a polynucleotide of the present invention, preferably the nucleotide sequence of SEQ ID NO:1, 3, or a fragment thereof;

(b) a nucleotide sequence complementary to that of (a);

(c) a polypeptide of the present invention, preferably the polypeptide of SEQ ID NO:2, 4 or a fragment thereof; or (d) an antibody to a polypeptide of the present invention, preferably to the polypeptide of SEQ ID NO:2, 4.

It will be appreciated that in any such kit, (a), (b), (c) or (d) may comprise a substantial component. Such a kit will be of use in diagnosing a disease or susceptibility to a disease, among others.

This invention also relates to the use of polynucleotides of the present invention as diagnostic reagents. Detection of a mutated form of a polynucleotide of the invention, preferable, SEQ ID NO:1, 3 which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR. As an example, PCR primers complementary to a polynucleotide encoding BASB006 polypeptide can be used to identify and analyze mutations.

The invention further provides primers with 1, 2, 3 or 4 nucleotides removed from the 5' and/or the 3' end. These primers may be used for, among other things, amplifying BASB006 DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing disease, preferably bacterial infections, more preferably infections caused by *Neisseria meningitidis,* comprising determining from a sample derived from an individual, such as a bodily material, an increased level of expression of polynucleotide having a sequence of SEQ ID NO:1, 3. Increased or decreased expression of a BASB006 polynucleotide can be measured using any on of the methods well known in the art for the quantitation of polynucleotides, such as, for example, amplification. PCR, RT-PCR, RNase protection, Northern blotting, spectrometry and other hybridization methods.

In addition, a diagnostic assay in accordance with the invention for detecting over-expression of BASB006 polypeptide compared to normal control tissue samples may be used to detect the presence of an infection, for example. Assay techniques that can be used to determine levels of a BASB006 polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

The polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as using hybridization or nucleic acid amplification, using a probe obtained or derived from a bodily sample, to determine the presence of a particular polynucleotide sequence or related sequence in an individual. Such a presence may indicate the presence of a pathogen, particularly *Neisseria meningitidis,* and may be useful in diagnosing and/or prognosing disease or a course of disease. A grid comprising a number of variants of the polynucleotide sequence of SEQ ID NO:1, 3 are preferred. Also preferred is a grid comprising a number of variants of a polynucleotide sequence encoding the polypeptide sequence of SEQ ID NO:2, 4.

Antibodies

The polypeptides and polynucleotides of the invention or variants thereof, or cells expressing the same can be used as immunogens to produce antibodies immunospecific for such polypeptides or polynucleotides respectively.

In certain preferred embodiments of the invention there are provided antibodies against BASB006 polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., *Nature* 256: 495–497 (1975); Kozbor et al., *Immunology Today* 4: 72 (1983); Cole et al., pg. 77–96 in *MONO-CLONAL ANTIBODIES AND CANCER THERAPY,* Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms or animals, such as other mammals. may be used to express humanized antibodies immunospecific to the polypeptides or polynucleotides of the invention.

Alternatively, phage display technology may be utilized to select antibody genes with binding activities towards a polypeptide of the invention either from repertoires of PCR amplified v-genes of lymphocytes from humans screened for possessing anti-BASB006 or from naive libraries (McCafferty, et al., (1990), Nature 348 552–554; Marks. et al., (1992) *Biotechnology* 10, 779–783). The affinity of these antibodies can also be improved by, for example, chain shuffling (Clackson et al., (1991) *Nature* 352: 628).

The above-described antibodies may be employed to isolate or to identify clones expressing the polypeptides or polynucleotides of the invention to purify the polypeptides or polynucleotides by, for example, affinity chromatography.

Thus, among others, antibodies against BASB006-polypeptide or BASB006-polynucleotide may be employed to treat infections, particularly bacterial infections.

Polypeptide variants include antigenically, epitopically or immunologically equivalent variants form a particular aspect of this invention.

Preferably, the antibody or variant thereof is modified to make it less immunogenic in the individual. For example, if the individual is human the antibody may most preferably be "humanized," where the complimentarity determining region or regions of the hybridoma-derived antibody has been transplanted into a human monoclonal antibody, for example as described in Jones et al. (1986), *Nature* 321, 522–525 or Tempest et al., (1991) *Biotechnology* 9, 266–273.

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g, Coligan et al., *Current Protocols in Immunology* 1(2). Chapter 5 (1991).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention, to form a mixture, measuring BASB006 polypeptide and/or polynucleotide activity in the mixture, and comparing the BASB006 polypeptide and/or polynucleotide activity of the mixture to a standard. Fusion proteins, such as those made from Fc portion and BASB006 polypeptide, as hereinbefore described, can also be used for high-throughput screening assays to identify antagonists of the polypeptide of the present invention, as well as of phylogenetically and and/or functionally related polypeptides (see D. Bennett et al., J Mol Recognition, 8:52–58 (1995); and K. Johanson et al., J Biol Chem, 270(16):9459–9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring, secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of BASB006 polypeptides or polynucleotides, particularly those compounds that are bacteristatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising BASB006 polypeptide and a labeled substrate or ligand of such polypeptide is incubated in the absence or the presence of a candidate molecule that may be a BASB006 agonist or antagonist. The ability of the candidate molecule to agonize or antagonize the BASB006 polypeptide is reflected in decreased binding of the labeled ligand or decreased production of product from such substrate. Molecules that bind gratuitously, i.e., without inducing the effects of BASB006 polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to calorimetric labeled substrate converted into product, a reporter gene that is responsive to changes in BASB006 polynucleotide or polypeptide activity, and binding assays known in the art.

Another example of an assay for BASB006 agonists is a competitive assay that combines BASB006 and a potential agonist with BASB006-binding molecules, recombinant BASB006 binding molecules, natural substrates or ligands, or substrate or ligand mimetics, under appropriate conditions for a competitive inhibition assay. BASB006 can be labeled, such as by radioactivity or a colorimetric compound, such that the number of BASB006 molecules bound to a binding molecule or converted to product can be determined accurately to assess the effectiveness of the potential antagonist.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing BASB006-induced activities, thereby preventing the action or expression of BASB006 polypeptides and/or polynucleotides by excluding BASB006 polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56:560 (1991); *OLIGODEOXYNUCLE-OTIDES AS ANTISENSE INHIBITORS OF GENE EXPRESSION,* CRC Press, Boca Raton, Fla. (1988), for a description of these molecules). Preferred potential antagonists include compounds related to and variants of BASB006.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering and to the use thereof for drug screening diagnosis and therapy. A further aspect of the invention also relates to polynucleotides encoding such fusion proteins. Examples of fusion protein technology can be found in International Patent Application Nos. WO94/29458 and WO94/22914.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds, to block bacterial adhesion between eukaryotic, preferably mammalian, extracellular matrix proteins and bacterial BASB006 proteins that mediate tissue damage and/or; to block the normal progression of pathogenesis in infections initiated other than by the implantation of in-dwelling devices or by other surgical techniques.

In accordance with yet another aspect of the invention, there are provided BASB006 agonists and antagonists, preferably bacteristatic or bactericidal agonists and antagonists.

The antagonists and agonists of the invention may be employed, for instance, to prevent, inhibit and/or treat diseases.

In a further aspect, the present invention relates to mimotopes of the polypeptide of the invention. A mimotope is a peptide sequence, sufficiently similar to the native peptide (sequentially or structurally), which is capable of being recognised by antibodies which recognise the native peptide; or is capable of raising antibodies which recognise the native peptide when coupled to a suitable carrier.

Peptide mimotopes may be designed for a particular purpose by addition, deletion or substitution of elected amino acids. Thus, the peptides may be modified for the purposes of ease of conjugation to a protein carrier. For example, it may be desirable for some chemical conjugation methods to include a terminal cysteine. In addition it may be desirable for peptides conjugated to a protein carrier to include a hydrophobic terminus distal from the conjugated terminus of the peptide, such that the free unconjugated end of the peptide remains associated with the surface of the carrier protein. Thereby presenting the peptide in a conformation which most closely resembles that of the peptide as found in the context of the whole native molecule. For example, the peptides may be altered to have an N-terminal cysteine and a C-terminal hydrophobic amidated tail. Alternatively, the addition or substitution of a D-stereoisomer form of one or more of the amino acids may be performed to create a beneficial derivative, for example to enhance stability of the peptide.

Alternatively, peptide mimotopes may be identified using antibodies which are capable themselves of binding to the polypeptides of the present invention using techniques such as phage display technology (EP 0 552 267 B1). This technique, generates a large number of peptide sequences which mimic the structure of the native peptides and are, therefore, capable of binding to anti-native peptide antibodies, but may not necessarily themselves share significant sequence homology to the native polypeptide.

Vaccines

Another aspect of the invention relates to a method for inducing an immunological response in an individual, particularly a mammal, preferably humans, which comprises inoculating the individual with BASB006 polynucleotide and/or polypeptide, or a fragment or variant thereof, adequate to produce antibody and/ or T cell immune response to protect said individual from infection, particularly bacterial infection and most particularly *Neisseria meningitidis* infection. Also provided are methods whereby such immunological response slows bacterial replication. Yet another aspect of the invention relates to a method of inducing immunological response in an individual which comprises delivering to such individual a nucleic acid vector, sequence or ribozyme to direct expression of BASB006 polynucleotide and/or polypeptide, or a fragment or a variant thereof, for expressing BASB006 polynucleotide and/or polypeptide, or a fragment or a variant thereof in vivo in order to induce an immunological response, such as, to produce antibody and/ or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect of the invention relates to an immunological composition that when introduced into an individual, preferably a human, capable of having induced within it an immunological response, induces an immunological response in such individual to a BASB006 polynucleotide and/or polypeptide encoded therefrom, wherein the composition comprises a recombinant BASB006 polynucleotide and/or polypeptide encoded therefrom and/or comprises DNA and/or RNA which encodes and expresses an antigen of said BASB006 polynucleotide, polypeptide encoded therefrom, or other polypeptide of the invention. The immunological response may be used therapeutically or prophylactically and may take the form of antibody immunity and/or cellular immunity, such as cellular immunity arising from CTL or CD4+T cells.

A BASB006 polypeptide or a fragment thereof may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, preferably further comprises an antigenic co-protein, such as lipoprotein D from *Haemophilus influenzae,* Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of the first protein.

Provided by this invention are compositions, particularly vaccine compositions, and methods comprising the polypeptides and/or polynucleotides of the invention and immunostimulatory DNA sequences, such as those described in Sato, Y. et al. Science 273:352 (1996).

Also, provided by this invention are methods using the described polynucleotide or particular fragments thereof which have been shown to encode non-variable regions of bacterial cell surface proteins, in polynucleotide constructs used in such genetic immunization experiments in animal models of infection with *Neisseria meningitidis.* Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *Neisseria meningitidis* infection, in mammals, particularly humans.

The invention also includes a vaccine formulation which comprises an immunogenic recombinant polypeptide and/or polynucleotide of the invention together with a suitable carrier, such as a pharmaceutically acceptable carrier. Since the polypeptides and polynucleotides may be broken down in the stomach, each is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteristatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

The vaccine formulation of the invention may also include adjuvant systems for enhancing the immunogenicity of the formulation. Preferably the adjuvant system raises preferentially a TH1 type of response.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4+ve T cell clones by Mosmann and Coffman (*Mosonzann, T. R. and Coffman, R. L.* (1989) *TH1and TH2 cells: different patterns of lymphokine secretion lead to different functional properties. Annual Review of Immunology,* 7, p145–173). Traditionally, TH1-type responses are associated with the production of the INF-γ and IL-2 cytokines by T-lymphocytes. Other cytokines often directly associated with the induction of TH1-type immune responses are not produced by T-cells, such as IL-12. In contrast, TH2- type responses are associated with the secretion of IL-4, IL-5, IL-6 and IL-I 13.

It is known that certain vaccine adjuvants are particularly suited to the stimulation of either TH1 or TH2- type cytokine responses. Traditionally the best indicators of the TH1 :TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a TH1-type adjuvant is one which preferentially stimulates isolated T-cell populations to produce high levels of TH1-type cytokines when re-stimulated with antigen in vitro, and promotes development of both CD8+ cytotoxic T lymphocytes and antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (European Patent number 0 689 454). 3D-MPL will be present in the range of 10 µg–100 µg preferably 25–50 µg per dose wherein the antigen will typically be present in a range 2–50 µg per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with a carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21:3D-MPL will typically be in the order of 1:10 to 10:1; preferably 1:5 to 5:1 and often substantially 1:1. The preferred range for optimal synergy is 2.5:1 to 1:13 D-MPL: QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 µg–200 µg, such as 10–100 µg, preferably 10 µg–50 µg per dose. Typically the oil in water will comprise from 2 to 10% squalene, from 2 to 10% alpha tocopherol and from 0.3 to 3% tween 80. Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The present invention also provides a polyvalent vaccine composition comprising a vaccine formulation of the invention in combination with other antigens, in particular antigens useful for treating cancers, autoimmune diseases and related conditions. Such a polyvalent vaccine composition may include a TH-1 inducing adjuvant as hereinbefore described.

While the invention has been described with reference to certain BASB006 polypeptides and polynucleotides, it is to be understood that this covers fragments of the naturally occurring polypeptides and polynucleotides, and similar polypeptides and polynucleotides with additions, deletions or substitutions which do not substantially affect the immunogenic properties of the recombinant polypeptides or polynucleotides.

The antigen can also be delivered in the form of whole bacteria (dead or alive) or as subcellular fractions, these possibilities do include *N. meningitidis* itself.

Compositions, Kits and Administration

In a further aspect of the invention there are provided compositions comprising a BASB006 polynucleotide and/or a BASB006 polypeptide for administration to a cell or to a multicellular organism.

The invention also relates to compositions comprising a polynucleotide and/or a polypeptide discussed herein or their agonists or antagonists. The polypeptides and polynucleotides of the invention may be employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides, polynucleotides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides, polynucleotides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, solutions, powders and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

The dosage range required depends on the choice of peptide, the route of administration, the nature of the formulation, the nature of the subject's condition, and the judgment of the attending practitioner. Suitable dosages, however, are in the range of 0.1–100 µg/kg of subject.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Sequence Databases, Sequences in a Tangible Medium, and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as the GCG program package.

Also provided by the invention are methods for the analysis of character sequences or strings, particularly genetic sequences or encoded protein sequences. Preferred methods of sequence analysis include, for example, methods of sequence homology analysis, such as identity and similarity analysis, DNA, RNA and protein structure analysis, sequence assembly, cladistic analysis, sequence motif analysis, open reading frame determination, nucleic acid base calling, codon usage analysis, nucleic acid base trimming, and sequencing chromatogram peak analysis.

A computer based method is provided for performing homology identification. This method comprises the steps of: providing a first polynucleotide sequence comprising the sequence of a polynucleotide of the invention in a computer readable medium; and comparing said first polynucleotide sequence to at least one second polynucleotide or polypeptide sequence to identify homology.

A computer based method is also provided for performing homology identification, said method comprising the steps of: providing a first polypeptide sequence comprising the sequence of a polypeptide of the invention in a computer readable medium; and comparing said first polypeptide sequence to at least one second polynucleotide or polypeptide sequence to identify homology.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

DEFINITIONS

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Mololecular, Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey. 1994; *Sequence Analysis in Molecular Biology,* von Heine, G., Academic Press, 1987; and *Sequence Analysis Primer,* Gribskov, M. and Devereux, J., eds., M Stockton Press. New York, 1991; and Carillo, H., and Lipman, D., SIAM *J. Applied Math.,* 48: 1073 (1988). Methods to determine identity are designed to give the largest match between the sequences tested. Moreover, methods to determine identity are codified in publicly available computer programs. Computer program methods to determine identity between two sequences include, but are not limited to the GAP program in the GCG program package (Devereux, J., et al., *Nucleic Acids Research* 12(1): 387 (1984)), BLASTP, BLASTN (Altschul, S. F. et al., *J. Molec. Biol.* 215: 403–410 (1990), and FASTA( Pearson and Lipman Proc. Natl. Acad. Sci. USA 85; 2444–2448 (1988). The BLAST family of programs is publicly available from NCBI and other sources (*BLAST Manual,* Altschul, S., et al., NCBI NLM NIH Bethesda, Md. 20894; Altschul, S., et al., *J. Miol. Biol.* 215: 403–410 (1990). The well known Smith Waterman algorithm may also be used to determine identity.

Parameters for polypeptide sequence comparison include the following:

Algorithm: Needleman and Wunsch, J. Mol Biol. 48: 443–453 (1970)

Comparison matrix: BLOSSUM62 from Henikoff and Henikoff,

Proc. Natl. Acad. Sci. USA. 89:10915–10919 (1992)

Gap Penalty: 8

Gap Length Penalty: 2

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:

Algorithm: Needleman and Wunsch, J. Mol Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \cdot y)$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:1, that is it may be 100% identical, or it may include up to a certain integer number of nucleic acid alterations as compared to the reference sequence such that the percent identity is less than 100% identity. Such alterations are selected from the group consisting of at least one nucleic acid deletion substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leq x_n - (x_n \cdot y),$$

wherein $n_n$ is the number of nucleic acid alterations, $x_n$ is the total number of nucleic acids in SEQ ID NO:1, y is, for instance 0.70 for 70%, 0.80 for 80%, 0.85 for 85% etc., · is the symbol for the multiplication operator, and wherein any non-integer product of $X_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion. substitution, including conservative and non-conservative substitution, or insertion, and wherein said alterations may occur at the amino- or carboxy-terninal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Individual(s)," when used herein with reference to an organism, means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Polynucleotide(s)" generally refers to any polyribonucleotide or polydeoxyribonucleotide, which may be unmodified RNA or DNA or modified RNA or DNA including single and double-stranded regions.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Disease(s)" means any disease caused by or related to infection by a bacteria, including, for example, upper respiratory tract infection, invasive bacterial diseases, such as bacteremia and meningitis.

EXAMPLES

The examples below are carried out using standard techniques, which are well known and routine to those of skill in the art except where otherwise described in detail. The examples are illustrative, but do not limit the invention.

Example 1

Discovery and Confirmatory DNA Sequencing of the BASB006 Gene from two N. meninigitidis Strains A: BASB006 in N. meningitidis serogroup B strain ATCC13090.

The BASB006 gene disclosed in SEQ ID NO:1 was first discovered in the Incyte PathoSeq database containing unfinished genomic DNA sequences of the *N. meningitidis* strain ATCCI13090. The translation of the BASB006 polynucleotide sequence, shown in SEQ ID NO:2, showed significant similarity (56% identity in a 1455 amino acids overlap) to the Hap protein of *Haemophilis influenzae,* a polypeptide reported previously to function as an adhesin. The sequence of the BASB006 gene was confirmed experimentally. For this purpose, genomic DNA was extracted from $10^{10}$ cells of the *N.meningitidis* cells (strain ATCC 13090) using the QIAGEN genomic DNA extraction kit (Qiagen Gmbh), and 1 μg of this material was submitted to Polymerase Chain Reaction DNA amplification using primers Hap01 (5'-GGG GGC TAG CAA AAC AAC CGA CAA ACG GAC AAC C-3') [SEQ ID NO:5] and Hap02 (5'-GGG GAA GCT TCC AGC GGT AGC GGT AGC CTA ATT TGA TGC C-3') [SEQ ID NO:6]. This PCR product was gel-purified and subjected to DNA sequencing using the Big Dye Cycle Sequencing kit (Perkin-Elmer) and an ABI 373A/PRISM DNA sequencer. DNA sequencing was performed on both strands with a redundancy of 2 and the full-length sequence was assembled using the SeqMan program from the DNASTAR Lasergene software package The resulting DNA sequence turned out to be 100 % identical to SEQ ID NO:1.

B: BASB006 in *N. meningitidis* serogroup B strain H44/76.

The sequence of the BASB006 gene was also determined in another *N. meningitidis* serogroup B strain, the strain H144/76. For this purpose, genomic DNA was extracted from the *N. meningitidis* strain H44/76 using the experimental conditions presented in Example 1. This material (1 μg) was then submitted to Polymerase Chain Reaction DNA amplification using primers Hap01 and Hap02 specific for the BASB006 gene. A 4389bp DNA fragment was obtained, digested by the NheI/HindIII restriction endonucleases and inserted into the corresponding sites of the pET-24b cloning/expression vector (Novagen) using standard molecular biology techniques (Molecular Cloning,a Laboratory Manual, Second Edition, Eds: Sambrook, Fritsch & Maniatis, Cold Spring Harbor press 1989). Recombinant pET-24b/BASB006 was then submitted to DNA sequencing using the Big Dyes kit (Applied biosystems) and analyzed on a ABI 373/A DNA sequencer in the conditions described by the supplier. As a result, the polynucleotide and deduced polypeptide sequences, referred to as SEQ ID NO:3 and SEQ ID NO:4 respectively, were obtained. Using the PILEUP program from the GCG package, an alignment of the polynucleotide sequences of SEQ ID NO:1 and 3 was performed, and is displayed in FIG. 1; their level of identity amounts to 97.8 %, as determined by the GAP program. Using the same PILEUP program, an alignment of the polypeptide sequences of SEQ ID NO:2 and 4 was performed, and is displayed in FIG. 2; their level of identity amounts to 97.0%, as determined by the GAP program.

Taken together, these data indicate strong sequence conservation of the BASB006 gene among the two *N.meningitidis* serogroup B strains.

Example 2

Expression and Purification of Recombinant BASB006 Protein in *Escherichia coli*

The construction of the pET-24b/BASB006 cloning/expression vector was described in Example 1B. This vector harbours the BASB006 gene isolated from the strain H44/76 in fusion with a stretch of 6 histidine residues, placed under the control of the strong bacteriophage T7 gene 10 promoter. For expression study, this vector was introduced into the *Escherichia coli* strain BL21 DE3 (Novagen), in which, the gene for the T7 polymerase is placed under the control of the isopropyl-beta-D thiogalactoside (IPTG)-regulatable lac promoter. Liquid cultures (100 ml) of the BL21 DE-3 [pET-24b/BASB006] *E. coli* recombinant strain were grown at 37° C. under agitation until the optical density at 600 nm (OD600) reached 0.6. At that time-point, IPTG was added at a final concentration of 1 mM and the culture was grown for 4 additional hours. The culture was then centrifuged at 10,000 rpm and the pellet was frozen at −20° C. for at least 10 hours. After thawing, the pellet was resuspended during 30 min at 25° C. in buffer A (6M guanidine hydrochloride, 0.1M NaH2PO4, 0.01M Tris, pH 8.0), passed three-times through a needle and clarified by centrifugation (20000 rpm, 15 min). The sample was then loaded at a flow-rate of 1 ml/min on a Ni2+-loaded Hitrap column (Pharmacia Biotech). After passsage of the flowthrough, the column was washed succesively with 40 ml of buffer B (8M Urea, 0.1M NaH2PO4, 0.01M Tris, pH 8.0), 40 ml of buffer C (8M Urea, 0.1M NaH2PO4, 0.01M Tris, pH 6.3). The recombinant protein BASB006/His6 was then eluted from the column with 30 ml of buffer C (8M Urea, 0.1 M NaH2PO4, 0.01M Tris, pH 6.3) containing 500 mM of imidazole and 3 ml-size fractions were collected. In FIG. 3 substantially purified proteins were separated on a 4–20% gradient polyacrylamide gel under PAGE-SDS conditions and stained with Coomassie Blue R250. The sample loaded on the gel corresponded to protein fractions enriched (more than 80%) in BASB006 (lane 1 and 2) and a molecular weight marker (MW). As shown in FIG. 3, a highly enriched (Purity estimated to more than 90% pure in coomassie staining) BASB006/His6 protein, migrating at 170 kDa (estimated relative molecular mass), was eluted from the column. This polypeptide was reactive against a mouse monoclonal antibody raised against the 5-histidine motif. Taken together, these data indicate that the BASB006 gene can be expressed and purified under a recombinant form (BASB006/His6) in *E.coli*.

Example 3

Immunization of Mice with Recombinant BASB006 and Recognition of the BASB006 Polypeptide on Different *N. meningitidis* Serogroup B Strains by Western Blotting.

Partially purified recombinant BASB006 expressed in *E. coli* has been injected three times in BALB/C mice on days 0, 14 and 28 (10 animals/group). Animals were injected by the subcutaneous route with 5 µg of antigen r formulated in SB62 emulsion containing 5 µg MPL, and 1 µpg QS21 per dose. Mice were bled on days 29 (15 days Post II) and 35 (6 days Post III) in order to detect specific anti-BASB006 antibodies. Specific anti-BASB006 antibodies were measured on pooled sera (from 10 mice/group) by western-blotting on six different *Neisseria meningitidis* serogroup B strains (FIG. 4).

The six different *Neisseria meningitidis* B strains are: H44/76 (B:15:P1.7, 16, lineage ET-5), M97 250987 (B:4:P1.15), BZ10 (B:2b:P1.2, lineage A4), BZ198 (B:NT*:-, lineage 3), and EG328 (B:NT*, lineage ST-18), and on partially purified recombinant BASB006 protein (mixed with two other candidate antigens). (*: NT: Not Typed).

Briefly, 15 µl (>10$^8$ cells/lane) of each sample treated with sample buffer (10 min at 95° C.) are put into a SDS-PAGE gradient gel (Tris-glycine 4–20%, Novex, code n°EC60252). Electrophoretic migration occurs at 125 volts for 90 min. Afterwards, proteins are transferred to a nitrocellulose sheet (0.45 µm, Bio-rad code n° 162–0114) at 100 volts for 1 hour using a Bio-rad Trans-blot system (code n°170–3930). The filter was blocked with PBS-0.05 % Tween 20 overnight at room temperature, before incubation with the mice sera containing the anti-BASB006 antibodies. These sera are diluted 100 times in PBS-0.05 % Tween 20. and incubated on the nitrocellulose sheet for two hours at room temperature with gentle shaking, using a mini-blotter system (Miniprotean. Bio-rad code n° 170–4017). After three repeated washing steps in PBS-0.05% Tween 20 for 5 min., the nitrocellulose sheet is incubated at room temperature for 1 hour under gentle shaking with the appropriate conjugate (biotinylated anti-mouse Ig antibodies from sheep, Amersham code n°RPN1001) diluted at 1/500 in the same washing buffer. The membrane is washed three times as previously, and incubated for 30 min. with agitation using the streptavidin-peroxidase complex (Amersham code n°1051) diluted at 1/1000 in the washing buffer. After the last three repeated washing steps, the revelation occurs during the 20 min incubation time in a 50 ml solution containing 30 mg 4-chloro-1-naphtol (Sigma), 10 ml methanol, 40 ml PBS, and 30 µl of $H_2O_2$. The staining is stopped while washing the membrane several times in distillated water.

Figure 4:
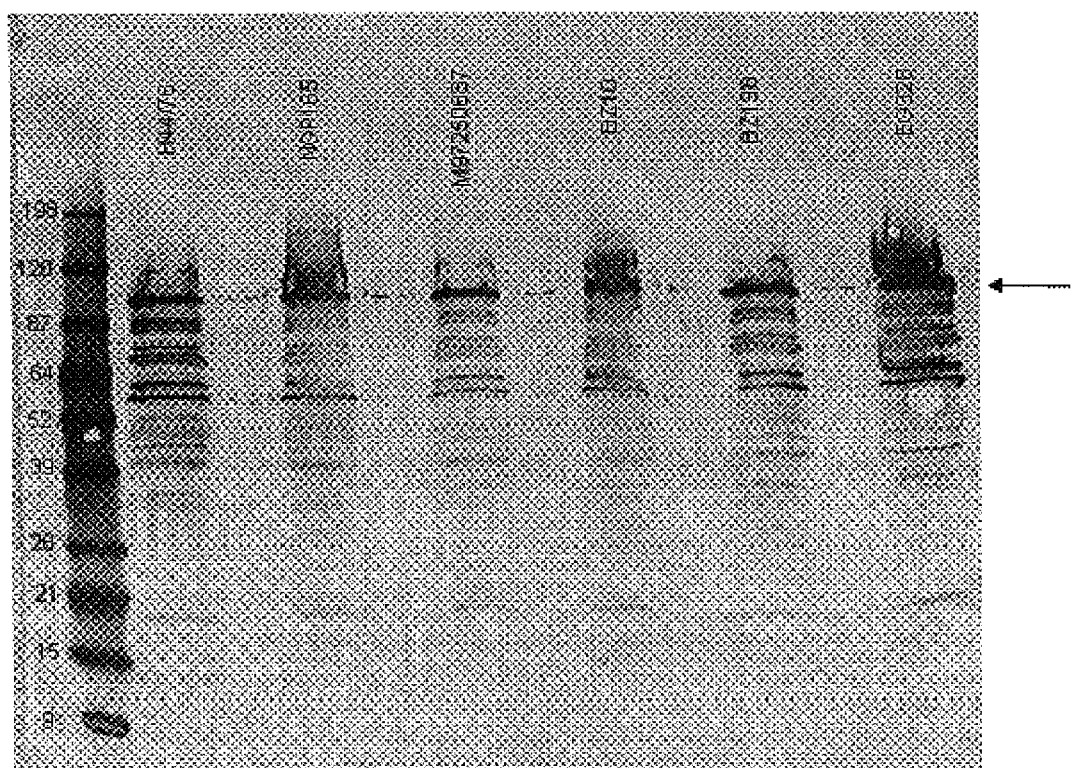
FIG. 4 shows a Western-blot of partially purified recombinant BASB006 protein probed with mice sera containing anti-BASB006 antibodies.

FIG. 4 shows recognition of the native BASB006 protein from several *Neisseria meningitidis* serogroup B strains by sera from immunized mice. Results illustrated in FIG. 4 show that all strains tested present a band around 95–100 kD (see arrow), which is probably the extracellular part of the BASB006 protein (after cleavage of the intact molecule into two pieces, which is known to occur in the *H. influenzae* Hap protein). This means that the BASB006 protein is probably expressed in most of the *Neisseria meningitidis* serogroup B strains. All other bands could be antibodies directed against degradation products, or against cross-reacting antigens between *E. coli* and *Neisseria meningitidis* B strains, as the preparation used for immunization still contained *E. coli* contaminants.

Example 4

Presence of anti-BASB006 Antibodies in Sera from Human Convalescent Patients

In this test, human convalescent sera were tested by western-blotting for recognition of the purified recombinant BASB006 protein.

5 µg of partially purified BASB006 protein mixed with two other *Neisseria meningitidis* serogroup B proteins are put into a SDS-PAGE gradient gel (4–20%, Novex, code n°EC60252) for electrophoretic migration. Proteins are transferred to nitrocellulose sheet (0.45 µm, Bio-rad code n° 162–0114) at 100 volts for 1 hour using a Bio-rad Trans-blot system (code n°170–3930). Afterwards, the filter is blocked with PBS-0.05% Tween 20 overnight at room temperature, before incubation with the human sera. These sera are diluted 100 times in PBS-0.05% Tween 20. and incubated on the nitrocellulose sheet for two hours at room temperature with gentle shaking, using a mini-blotter system (Miniprotean, Bio-rad code n° 170–4017). After three repeated washing steps in PBS-0.05 % Tween 20 for 5 min., the nitrocellulose sheet is incubated at room temperature for 11 hour under gentle shaking with the appropriate conjugate (biotinylated anti-human Ig antibodies, from sheep, Amersham code n°RPN1003) diluted at 1/500 in the same washing buffer. The membrane is washed three times as previously, and incubated for 30 min with agitation using the streptavidin-peroxidase complex (Amersham code n°1051) diluted at 1/1000 in the washing buffer. After the last three repeated washing steps, the revelation occurs during the 20 min incubation time in a 50 ml solution containing 30 µg 4-chloro-1-naphtol (Sigma), 10 ml methanol, 40 ml of ultra-pure water, and 30µl of $H_2O_2$. The staining is stopped while washing the membrane several times in distillated water.

Figure 5:
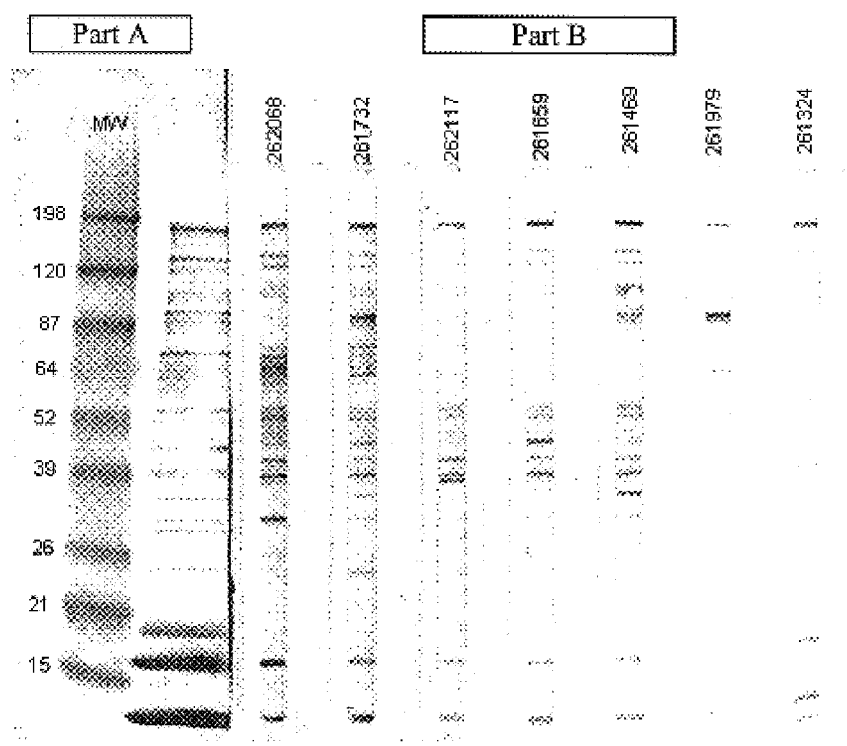
FIG. 5 shows a Western-blot of partially purified recombinant BASB006 protein probed with human convalescent sera and mice sera.

Results illustrated in FIG. 5 (Part B) show that all convalescent sera react against the intact BASB006 protein at around 160 kD, while 3 out of 7 convalescent sera are reacting against the possible processed BASB006 protein (+/−95–100 kD). The BASB006 bands are clearly visible at these two molecular weights ( 95–100 and 160 kD). In part A of the western-blot, it can be seen that mice sera (mixture of specific antibodies against three different Ag candidates) recognize the intact recombinant BASB006 protein at the same molecular weight, while at the lower MW, it is more difficult to discriminate which of the two bands around 95 kD is related to the processed BASB006 protein.

Deposited Materials

A deposit containing a *Neisseria meningitidis* Scrogroup B strain has been deposited with the American Type Culture Collection (herein "ATCC") on June 22, 1997 and assigned deposit number 13090. The deposit was described as *Neisseria meningitidis* (Albrecht and Ghon) and is a freeze-dried, 1.5–2.9 kb insert library constructed from *N. meningitidis* isolate. The deposit is described in Int. Bull. Bacteriol. Nomencl. Taxon. 8: 1–15 (1958).

The *Neissria meningitidis* strain deposit is referred to herein as "the deposited strain" or as "the DNA of the deposited strain."

The deposited strain contains the full length BASB006 gene. The sequence of the polynucleotides contained in the deposited strain, as well as the amino acid sequence of any polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

What is claimed is:

1. An isolated polypeptide comprising SEQ ID NO:2.

2. The isolated polypeptide of claim 1, wherein the isolated polypeptide consists of SEQ ID NO:2.

3. A fusion protein comprising the isolated polypeptide of claim 1 and a polypeptide selected to:
    (a) provide T helper epitopes or
    (b) facilitate purification from a recombinant expression system.

4. An immunogenic composition comprising the isolated polypeptide of claim 1 and a pharmaceutically acceptable carrier.

5. The immunogenic composition of claim 4, wherein the composition comprises at least one other *Neisseria meningitidis* antigen.

6. An isolated polypeptide comprising SEQ ID NO:4.

7. The isolated polypeptide of claim 6, wherein the isolated polypeptide consists of SEQ ID NO:4.

8. A fusion protein comprising the isolated polypeptide of claim 6 and a polypeptide selected to:
   (a) provide T helper epitopes or
   (b) facilitate purification from a recombinant expression system.

9. An immunogenic composition comprising the isolated polypeptide of claim 6 and a pharmaceutically acceptable carrier.

10. The immunogenic composition of claim 9, wherein the composition comprises at least one other *Neisseria meningitidis* antigen.

* * * * *

SEQUENCE LISTING

```
<160> NUMBER OF SEQ ID NOS: 6

<210> SEQ ID NO 1
<211> LENGTH: 4365
<212> TYPE: DNA
<213> ORGANISM: Bacteria

<400> SEQUENCE: 1
atgaaaacaa ccgacaaacg gacaaccgaa acacaccgca aagccccgaa aaccggtcgc         60
atccgcttct cgcctgctta cttagccata tgcctgtcgt tcggcattct tccccaagcc        120
tgggcgggac acacttattt cggcatcaac taccaatact atcgcgactt tgccgaaaat        180
aaaggcaagt ttgcagtcgg ggcgaaagat attgaggttt acaacaaaaa agggagttg        240 gtcggcaaat caatgacaaa agccccgatg attgatttt ctgtggtgtc gcgtaacggc        300
gtggcggcat tggtgggcga tcaatatatt gtgagcgtgg cacataacgg cggctataac        360
aacgttgatt ttggtgcgga gggaagcaat cccgatcagc accgttttc ttatcaaatt        420 gtgaaaagaa ataattataa agcagggact aacggtcatc cttatggtgg cgattatcat        480
atgccgcgtt tacataaatt tgtaaccgat gcagaacctg ttgaaatgac cagttatatg        540
gatgggcgga aatatatcga tcaaaataat taccctgacc gtgttcgtat tggggcaggc        600
aggcaatatt ggcgatctga tgaagatgag cccaataacc gcgaaagttc atatcatatt        660
gcaagtgcgt attcttggct cgttggtggc aataccttg cacaaaatgg atcaggtggt        720
ggcacagtca acttaggtag tgaaaaaatt aaacatagcc catatggttt tttaccaaca        780
ggaggctcat ttggcgacag tggctcacca atgtttatct atgatgccca aaagcaaaag        840
tggttaatta atgggtatt gcaaacgggc aacccctata taggaaaaag caatggcttc        900
cagctggttc gtaaagattg gttctatgat gaaatctttg ctgagatac ccattcagta        960 ttctacgaac cacatcaaaa tgggaaatac actttcacg acaataataa tggcacagga       1020
```

```
aaaatcaatg ccaaacatga acacaattct ctgcctaata gattaaaaac acgaaccgtt    1080
caattgttta atgtttcttt atccgagaca gcaagagaac ctgtttatca tgctgcaggt    1140
ggtgtcaaca gttatcgacc cagactgaat aatggagaaa atatttcctt tattgacgaa    1200
ggaaaaggcg aattgatact taccagcaac atcaatcaag gtgctggagg attatatttc    1260
caaggagatt ttacggtctc gcctgaaaat aacgaaacgt ggcaaggtgc gggcgttcat    1320
atcagtgaag acagtaccgt tacttggaaa gtaaacggcg tggcaaacga ccgcctgtcc    1380
aaaatcggca aaggcacgct gcacgttcaa gccaaagggg aaaaccaagg ctcgatcagc    1440
gtgggcgacg gtaaagttat tttagatcaa caagcagatg aaaataataa aaaacaagcc    1500
tttagtgaaa tcggcttggt cagcggcagg ggtacggtgc aactgaatgc cgataatcag    1560
ttcaaccccg acaaactcta tttcggcttt cgcggcggac gtttggattt gaacgggcat    1620
tcgctttcgt tccaccgtat tcaaaatacc gatgaagggg cgatgattgt caaccacaat    1680
caagacaaag aatccaccgt taccattaca ggcaataaag atattgctac aaccggcaat    1740
aacaacagct tggatagcaa aaaagaaatt gcctacaacg gttggtttgg cgagaaagat    1800
acgaccaaaa cgaacgggcg gctcaacctt gtttaccagc ccgccgcaga agaccgcacc    1860
ctgctgcttt ccggcggaac aaatttaaac ggtaacatca cgcaaacaaa cggcaaactg    1920
tttttcagcg gcagaccgac accgcacgcc tacaatcatt taggaagcgg gtggtcaaaa    1980
atggaaggta tcccacaagg agaaatcgtg tgggacaacg actggatcaa ccgcacgttt    2040
aaagcggaaa atttccatat tcagggcggg caggcggtga tttcccgcaa tgttgccaaa    2100
gtggaaggcg attggcattt gagcaatcac gcccaagcag tttttggtgt cgcaccgcat    2160
caaagccaca caatctgtac acgttcggac tggacgggtc tgacaaattg tgtcgaaaaa    2220
accattaccg acgataaagt gattgcttca ttgactaaga ccgacatcag cggcaatgtc    2280
agccttgccg atcacgctca tttaaatctc acagggcttg ccacactcaa cggcaatctt    2340
agtgcaaatg gcgatacacg ttatacagtc agccacaacg ccacccaaaa cggcgacctt    2400
agcctcgtgg gcaatgccca agcaacattt aatcaagcca cattaaacgg caacacatcg    2460
gcttcgggca atgcttcatt taatctaagc aacaacgccg tacaaaacgg cagtctgacg    2520 cttttccggca acgctaaggc aaacgtaagc cattccgcac tcaacggtaa tgtctcccta    2580
gccgataagg cagtattcca ttttgaaagc agccgcttta ccggacaaat cagcggcagc    2640
aaggatacgg cattacactt aaaagacagc gaatggacgt tgccgtcagg cacggaatta    2700
ggcaatttaa accttgacaa cgccaccatt acactcaatt ccgcctatcg ccacgatgcg    2760
gcagggggcg aaaccggcag tgcgacagat gcgccgcgcc gccgttcgcg ccgttcccta    2820
ttatccgtta cacctccggc ttcggcagaa tcccatttca acacgctgac ggtaaacggc    2880
aaattgaacg gtcagggaac attccgcttt atgtcggaac tcttcggcta ccgaagcgac    2940
aaattgaagc tggcggaaag ttccgaaggc acttacacct tggcggtcaa caataccggc    3000
aacgaacccg taagcctcga tcaattgacg gtagtgaagg ggaaagacaa caaaccgctg    3060
tccgaaaacc ttaatttcac cctgcaaaac gaacacgtcg atgccggcgc gtggcgttac    3120
caactcatcc gcaaagacgg cgagttccgc ctgcataatc cggtcaaaga acaagagctt    3180
tccgacaaac tcggcaaggc agaagccaaa aaacaggcgg gaaaagacaa cgcgcaaagc    3240
cttgacgcgc tgattgcggc cggcgcgat gccgtcgaaa agacagaaag cgttgccgaa    3300
ccggcccggc aggcaggcgg ggaaaatgtc ggcattatgc aggcggagga agagaaaaaa    3360
```

-continued

```
cgggtgcagg cggataaaga caccgccttg gcgaaacagc gcgaagggaa acccggccg     3420
gctaccaccg ccttcccccg cgcccgccgc gcccgccggg atttgccgca accgcagccc    3480
caaccgcaac cccaaccgca gcgcgacctg atcagccgtt atgccaatag cggtttgagt    3540
gaattttccg ccacgctcaa cagcgttttc gccgtacagg acgaattaga ccgcgtattt    3600
gccgaagacc gccgcaacgc cgtttggaca agcggcatcc gggacaccaa acactaccgt    3660
tcgcaagatt tccgcgccta ccgccaacaa accgacctgc gccaaatcgg tatgcagaaa    3720
aacctcggca gcgggcgcgt cggcatcctg ttttcgcaca accggaccga aaacaccttc    3780
gacgacggca tcggcaactc ggcacggctt gcccacggcg ccgttttcgg caatacggc     3840
atcggcaggt tcgacatcgg catcagcacg ggcgcgggtt ttagcagcgg cagtctttca    3900
gacgacatcg gaagcaaaat ccgccgccgc gtgctgcatt acggcattca ggcacgatac    3960
cgcgccggtt tcggcggatt cggcatcgaa ccgcacatcg gcgcaacgcg ctatttcgtc    4020
caaaagcgg attaccgcta cgaaaacgtc aatatcgcca ccccggcct tgcgttcaac      4080
cgctaccgcg cgggcattaa ggcagattat tcattcaaac cggcgcaaca catttccatc    4140
acgccttatt tgagcctgtc ctataccgat gccgcttcgg gcaaagtccg aacgcgcgtc    4200
aataccgccg tattggctca ggatttcggc aaaacccgca gtgcggaatg gggcgtaaac    4260
gccgaaatca aggtttcac gctgtccctc cacgctgccg ccgccaaagg cccgcaactg     4320
gaagcgcaac acagcgcggg catcaaatta ggctaccgct ggtaa                    4365
```

<210> SEQ ID NO 2
<211> LENGTH: 1454
<212> TYPE: PRT
<213> ORGANISM: Bacteria

<400> SEQUENCE: 2

```
Met Lys Thr Thr Asp Lys Arg Thr Thr Glu Thr His Arg Lys Ala Pro
  1               5                  10                  15

Lys Thr Gly Arg Ile Arg Phe Ser Pro Ala Tyr Leu Ala Ile Cys Leu
             20                  25                  30

Ser Phe Gly Ile Leu Pro Gln Ala Trp Ala Gly His Thr Tyr Phe Gly
         35                  40                  45

Ile Asn Tyr Gln Tyr Tyr Arg Asp Phe Ala Glu Asn Lys Gly Lys Phe
     50                  55                  60

Ala Val Gly Ala Lys Asp Ile Glu Val Tyr Asn Lys Lys Gly Glu Leu
 65                  70                  75                  80

Val Gly Lys Ser Met Thr Lys Ala Pro Met Ile Asp Phe Ser Val Val
                 85                  90                  95

Ser Arg Asn Gly Val Ala Ala Leu Val Gly Asp Gln Tyr Ile Val Ser
            100                 105                 110

Val Ala His Asn Gly Gly Tyr Asn Asn Val Asp Phe Gly Ala Glu Gly
        115                 120                 125

Ser Asn Pro Asp Gln His Arg Phe Ser Tyr Gln Ile Val Lys Arg Asn
    130                 135                 140

Asn Tyr Lys Ala Gly Thr Asn Gly His Pro Tyr Gly Gly Asp Tyr His
145                 150                 155                 160

Met Pro Arg Leu His Lys Phe Val Thr Asp Ala Glu Pro Val Glu Met
                165                 170                 175

Thr Ser Tyr Met Asp Gly Arg Lys Tyr Ile Asp Gln Asn Asn Tyr Pro
            180                 185                 190

Asp Arg Val Arg Ile Gly Ala Gly Arg Gln Tyr Trp Arg Ser Asp Glu
```

-continued

```
            195                 200                 205
Asp Glu Pro Asn Asn Arg Glu Ser Ser Tyr His Ile Ala Ser Ala Tyr
    210                 215                 220

Ser Trp Leu Val Gly Gly Asn Thr Phe Ala Gln Asn Gly Ser Gly Gly
225                 230                 235                 240

Gly Thr Val Asn Leu Gly Ser Glu Lys Ile Lys His Ser Pro Tyr Gly
                245                 250                 255

Phe Leu Pro Thr Gly Gly Ser Phe Gly Asp Ser Gly Ser Pro Met Phe
            260                 265                 270

Ile Tyr Asp Ala Gln Lys Gln Lys Trp Leu Ile Asn Gly Val Leu Gln
        275                 280                 285

Thr Gly Asn Pro Tyr Ile Gly Lys Ser Asn Gly Phe Gln Leu Val Arg
    290                 295                 300

Lys Asp Trp Phe Tyr Asp Glu Ile Phe Ala Gly Asp Thr His Ser Val
305                 310                 315                 320

Phe Tyr Glu Pro His Gln Asn Gly Lys Tyr Thr Phe His Asp Asn Asn
                325                 330                 335

Asn Gly Thr Gly Lys Ile Asn Ala Lys His Glu His Asn Ser Leu Pro
            340                 345                 350

Asn Arg Leu Lys Thr Arg Thr Val Gln Leu Phe Asn Val Ser Leu Ser
        355                 360                 365

Glu Thr Ala Arg Glu Pro Val Tyr His Ala Ala Gly Val Asn Ser
    370                 375                 380

Tyr Arg Pro Arg Leu Asn Asn Gly Glu Asn Ile Ser Phe Ile Asp Glu
385                 390                 395                 400

Gly Lys Gly Glu Leu Ile Leu Thr Ser Asn Ile Asn Gln Gly Ala Gly
                405                 410                 415

Gly Leu Tyr Phe Gln Gly Asp Phe Thr Val Ser Pro Glu Asn Asn Glu
            420                 425                 430

Thr Trp Gln Gly Ala Gly Val His Ile Ser Glu Asp Ser Thr Val Thr
        435                 440                 445

Trp Lys Val Asn Gly Val Ala Asn Asp Arg Leu Ser Lys Ile Gly Lys
    450                 455                 460

Gly Thr Leu His Val Gln Ala Lys Gly Glu Asn Gln Gly Ser Ile Ser
465                 470                 475                 480

Val Gly Asp Gly Lys Val Ile Leu Asp Gln Gln Ala Asp Glu Asn Asn
                485                 490                 495

Lys Lys Gln Ala Phe Ser Glu Ile Gly Leu Val Ser Gly Arg Gly Thr
            500                 505                 510

Val Gln Leu Asn Ala Asp Asn Gln Phe Asn Pro Asp Lys Leu Tyr Phe
        515                 520                 525

Gly Phe Arg Gly Gly Arg Leu Asp Leu Asn Gly His Ser Leu Ser Phe
    530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
            580                 585                 590

Asn Gly Trp Phe Gly Glu Lys Asp Thr Thr Lys Thr Asn Gly Arg Leu
        595                 600                 605

Asn Leu Val Tyr Gln Pro Ala Ala Glu Asp Arg Thr Leu Leu Leu Ser
    610                 615                 620
```

-continued

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Gly Ser
            645                 650                 655

Gly Trp Ser Lys Met Glu Gly Ile Pro Gln Gly Glu Ile Val Trp Asp
            660                 665                 670

Asn Asp Trp Ile Asn Arg Thr Phe Lys Ala Glu Asn Phe His Ile Gln
            675                 680                 685

Gly Gly Gln Ala Val Ile Ser Arg Asn Val Ala Lys Val Glu Gly Asp
690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
            740                 745                 750

Lys Thr Asp Ile Ser Gly Asn Val Ser Leu Ala Asp His Ala His Leu
            755                 760                 765

Asn Leu Thr Gly Leu Ala Thr Leu Asn Gly Asn Leu Ser Ala Asn Gly
770                 775                 780

Asp Thr Arg Tyr Thr Val Ser His Asn Ala Thr Gln Asn Gly Asp Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asn Asn
            820                 825                 830

Ala Val Gln Asn Gly Ser Leu Thr Leu Ser Gly Asn Ala Lys Ala Asn
            835                 840                 845

Val Ser His Ser Ala Leu Asn Gly Asn Val Ser Leu Ala Asp Lys Ala
850                 855                 860

Val Phe His Phe Glu Ser Ser Arg Phe Thr Gly Gln Ile Ser Gly Ser
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
            900                 905                 910

Asn Ser Ala Tyr Arg His Asp Ala Ala Gly Ala Gln Thr Gly Ser Ala
            915                 920                 925

Thr Asp Ala Pro Arg Arg Ser Arg Arg Ser Leu Leu Ser Val Thr
930                 935                 940

Pro Pro Ala Ser Ala Glu Ser His Phe Asn Thr Leu Thr Val Asn Gly
945                 950                 955                 960

Lys Leu Asn Gly Gln Gly Thr Phe Arg Phe Met Ser Glu Leu Phe Gly
                965                 970                 975

Tyr Arg Ser Asp Lys Leu Lys Leu Ala Glu Ser Ser Glu Gly Thr Tyr
            980                 985                 990

Thr Leu Ala Val Asn Asn Thr Gly Asn Glu Pro Val Ser Leu Asp Gln
            995                 1000                1005

Leu Thr Val Glu Gly Lys Asp Asn Lys Pro Leu Ser Glu Asn Leu
    1010                1015                1020

Asn Phe Thr Leu Gln Asn Glu His Val Asp Ala Gly Ala Trp Arg Tyr
1025                1030                1035                1040

-continued

```
Gln Leu Ile Arg Lys Asp Gly Glu Phe Arg Leu His Asn Pro Val Lys
            1045                1050                1055

Glu Gln Glu Leu Ser Asp Lys Leu Gly Lys Ala Glu Ala Lys Lys Gln
    1060                1065                1070

Ala Gly Lys Asp Asn Ala Gln Ser Leu Asp Ala Leu Ile Ala Ala Gly
    1075                1080                1085

Arg Asp Ala Val Glu Lys Thr Glu Ser Val Ala Glu Pro Ala Arg Gln
    1090                1095                1100

Ala Gly Gly Glu Asn Val Gly Ile Met Gln Ala Glu Glu Lys Lys
1105                1110                1115                1120

Arg Val Gln Ala Asp Lys Asp Thr Ala Leu Ala Lys Gln Arg Glu Gly
            1125                1130                1135

Lys Thr Arg Pro Ala Thr Thr Ala Phe Pro Arg Ala Arg Arg Ala Arg
            1140                1145                1150

Arg Asp Leu Pro Gln Pro Gln Pro Gln Pro Gln Pro Gln Pro Gln Arg
            1155                1160                1165

Asp Leu Ile Ser Arg Tyr Ala Asn Ser Gly Leu Ser Glu Phe Ser Ala
            1170                1175                1180

Thr Leu Asn Ser Val Phe Ala Val Gln Asp Glu Leu Asp Arg Val Phe
1185                1190                1195                1200

Ala Glu Asp Arg Arg Asn Ala Val Trp Thr Ser Gly Ile Arg Asp Thr
            1205                1210                1215

Lys His Tyr Arg Ser Gln Asp Phe Arg Ala Tyr Arg Gln Gln Thr Asp
            1220                1225                1230

Leu Arg Gln Ile Gly Met Gln Lys Asn Leu Gly Ser Gly Arg Val Gly
            1235                1240                1245

Ile Leu Phe Ser His Asn Arg Thr Glu Asn Thr Phe Asp Asp Gly Ile
            1250                1255                1260

Gly Asn Ser Ala Arg Leu Ala His Gly Ala Val Phe Gly Gln Tyr Gly
1265                1270                1275                1280

Ile Gly Arg Phe Asp Ile Gly Ile Ser Thr Gly Ala Gly Phe Ser Ser
            1285                1290                1295

Gly Ser Leu Ser Asp Asp Ile Gly Ser Lys Ile Arg Arg Arg Val Leu
            1300                1305                1310

His Tyr Gly Ile Gln Ala Arg Tyr Arg Ala Gly Phe Gly Phe Gly
            1315                1320                1325

Ile Glu Pro His Ile Gly Ala Thr Arg Tyr Phe Val Gln Lys Ala Asp
            1330                1335                1340

Tyr Arg Tyr Glu Asn Val Asn Ile Ala Thr Pro Gly Leu Ala Phe Asn
1345                1350                1355                1360

Arg Tyr Arg Ala Gly Ile Lys Ala Asp Tyr Ser Phe Lys Pro Ala Gln
            1365                1370                1375

His Ile Ser Ile Thr Pro Tyr Leu Ser Leu Ser Tyr Thr Asp Ala Ala
            1380                1385                1390

Ser Gly Lys Val Arg Thr Arg Val Asn Thr Ala Val Leu Ala Gln Asp
            1395                1400                1405

Phe Gly Lys Thr Arg Ser Ala Glu Trp Gly Val Asn Ala Glu Ile Lys
            1410                1415                1420

Gly Phe Thr Leu Ser Leu His Ala Ala Ala Lys Gly Pro Gln Leu
1425                1430                1435                1440

Glu Ala Gln His Ser Ala Gly Ile Lys Leu Gly Tyr Arg Trp
            1445                1450
```

-continued

<210> SEQ ID NO 3
<211> LENGTH: 4374
<212> TYPE: DNA
<213> ORGANISM: Bacteria

<400> SEQUENCE: 3

| | | | | | |
|---|---|---|---|---|---|
| atgaaaacaa | ccgacaaacg | gacaaccgaa | acacaccgca | aagccccgaa | aaccggccgc | 60 |
| atccgcttct | cgcctgctta | cttagccata | tgcctgtcgt | tcggcattct | tccccaagcc | 120 |
| tgggcgggac | acacttattt | cggcatcaac | taccaatact | atcgcgactt | tgccgaaaat | 180 |
| aaaggcaagt | ttgcagtcgg | ggcgaaagat | attgaggttt | acaacaaaaa | agggagttg | 240 |
| gtcggcaaat | caatgacaaa | agccccgatg | attgattttt | ctgtggtgtc | gcgtaacggc | 300 |
| gtggcggcat | tggtgggcga | tcaatatatt | gtgagcgtgg | cacataacgg | cggctataac | 360 |
| aacgttgatt | tggtgcgga | aggaagaaat | cccgatcaac | atcgttttac | ttataaaatt | 420 |
| gtgaaacgga | ataattataa | agcagggact | aaaggccatc | cttatggtgg | cgattatcat | 480 |
| atgccgcgtt | tacataaatt | tgtcacagat | gcagaacctg | ttgaaatgac | cagttatatg | 540 |
| gatgggcgga | aatatatcga | tcaaaataat | taccctgacc | gtgttcgtat | tggggcaggc | 600 |
| aggcaatatt | ggcgatctga | tgaagatgag | cccaataacc | gcgaaagttc | atatcatatt | 660 |
| gcaagtgcgt | attcttggct | cgttggtggc | aatacctttg | cacaaaatgg | atcaggtggt | 720 |
| ggcacagtca | acttaggtag | tgaaaaaatt | aaacatagcc | catatggttt | tttaccaaca | 780 |
| ggaggctcat | ttggcgacag | tggctcacca | atgtttatct | atgatgccca | aaagcaaaag | 840 |
| tggttaatta | atggggtatt | gcaaacgggc | aacccctata | taggaaaaag | caatggcttc | 900 |
| cagctggttc | gtaaagattg | gttctatgat | gaaatctttg | ctggagatac | ccattcagta | 960 |
| ttctacgaac | cacgtcaaaa | tgggaaatac | tcttttaacg | acgataataa | tggcacagga | 1020 |
| aaaatcaatg | ccaaacatga | acacaattct | ctgcctaata | gattaaaaac | acgaaccgtt | 1080 |
| caattgttta | atgtttcttt | atccgagaca | gcaagagaac | ctgtttatca | tgctgcaggt | 1140 |
| ggtgtcaaca | gttatcgacc | cagactgaat | aatggagaaa | atatttcctt | tattgacgaa | 1200 |
| ggaaaaggcg | aattgatact | taccagcaac | atcaatcaag | gtgctggagg | attatatttc | 1260 |
| caaggagatt | ttacggtctc | gcctgaaaat | aacgaaacgt | ggcaaggtgc | gggcgttcat | 1320 |
| atcagtgaag | acagtaccgt | tacttggaaa | gtaaacggcg | tggcaaacga | ccgcctgtcc | 1380 |
| aaaatcggca | aggcacgct | gcacgttcaa | gccaaggggg | aaaaccaagg | ctcgatcagc | 1440 |
| gtgggcgacg | gtacagtcat | tttggatcag | caggcagacg | ataaaggcaa | aaacaagcc | 1500 |
| tttagtgaaa | tcggcttggt | cagcggcagg | ggtacggtgc | aactgaatgc | cgataatcag | 1560 |
| ttcaaccccg | acaaactcta | tttcggcttt | cgcggcggac | gtttggattt | aaacgggcat | 1620 |
| tcgctttcgt | tccaccgtat | tcaaaatacc | gatgaagggg | cgatgattgt | caaccacaat | 1680 |
| caagacaaag | aatccaccgt | taccattaca | ggcaataaag | atattgctac | aaccggcaat | 1740 |
| aacaacagct | tggatagcaa | aaaagaaatt | gcctacaacg | gttggtttgg | cgagaaagat | 1800 |
| acgaccaaaa | cgaacgggcg | gctcaacctt | gtttaccagc | cgccgcaga | agaccgcacc | 1860 |
| ctgctgcttt | ccggcggaac | aaatttaaac | ggcaacatca | cgcaaacaaa | cggcaaactg | 1920 |
| ttttcagcg | gcagaccaac | accgcacgcc | tacaatcatt | taaacgacca | ttggtcgcaa | 1980 |
| aaagagggca | ttccacgcgg | ggaaatcgtg | tgggacaacg | actggatcaa | ccgcacattt | 2040 |
| aaagcggaaa | acttccaaat | taaggcgga | caggcggtgg | tttcccgcaa | tgttgccaaa | 2100 |
| gtgaaaggcg | attggcattt | gagcaatcac | gcccaagcag | ttttttggtgt | cgcaccgcat | 2160 |

-continued

```
caaagccaca caatctgtac acgttcggac tggacgggtc tgacaaattg tgtcgaaaaa    2220
accattaccg acgataaagt gattgcttca ttgactaaga ccgacatcag cggcaatgtc    2280
gatcttgccg atcacgctca tttaaatctc acagggcttg ccacactcaa cggcaatctt    2340
agtgcaaatg gcgatacacg ttatacagtc agccacaacg ccacccaaaa cggcaacctt    2400
agcctcgtgg gcaatgccca agcaacattt aatcaagcca cattaaacgg caacacatcg    2460
gcttcgggca atgcttcatt taatctaagc gaccacgccg tacaaaacgg cagtctgacg    2520
ctttccggca acgctaaggc aaacgtaagc cattccgcac tcaacggtaa tgtctccccta   2580 gccgataagg cagtattcca ttttgaaagc agccgcttta ccggacaaat cagcggcggc    2640
aaggatacgg cattacactt aaaagacagc gaatggacgc tgccgtcagg cacggaatta    2700
ggcaatttaa accttgacaa cgccaccatt acactcaatt ccgcctatcg ccacgatgcg    2760
gcaggggcgc aaaccggcag tgcgacagat gcgccgcgcc gccgttcgcg ccgttcgcgc    2820
cgttccctat tatccgttac accgccaact tcggtagaat cccgtttcaa cacgctgacg    2880
gtaaacggca aattgaacgg tcagggaaca ttccgcttta tgtcggaact cttcggctac    2940
cgcagcgaca aattgaagct ggcggaaagt tccgaaggca cttacacctt ggcggtcaac    3000
aataccggca cgaacctgc aagccttgaa caattgacgg tagtggaagg aaaagacaac    3060
aaaccgctgt ccgaaaactt taatttcacc ttgcaaaacg aacacgtcga tgccggcgcg    3120
tggcgttacc aactcatccg caaagacggc gagttccgcc tgcataatcc ggtcaaagaa    3180
caagagcttt ccgacaaact cggcaaggca gaagccaaaa acaggcgga aaaagacaac    3240 gcgcaaagcc ttgacgcgct gattgcggcc gggcgcgatg ccgtcgaaaa gacagaaagc    3300
gttgccgaac cggcccggca ggcaggcggg gaaaatgtcg gcattatgca ggcggaggaa    3360
gagaaaaaac gggtgcaggc ggataaagac accgccttgg cgaaacagcg cgaagcggaa    3420
acccggccgc ctaccaccgc cttccccgc gcccgccgcg cccgccggga tttgccgcaa    3480
ctgcaacccc aaccgcagcc ccaaccgcag cgcgacctga tcagccgtta tgccaatagc    3540
ggtttgagtg aattttccgc cacgctcaac agcgttttcg ccgtacagga cgaattagac    3600
cgcgtatttg ccgaagaacg ccgcaacgcc gtttggacaa gcggcatccg ggacaccaaa    3660
cactaccgtt cgcaagattt ccgcgcctac cgccaacaaa ccgacctgcg ccaaatcggt    3720
atgcagaaaa acctcggcag cgggcgcgtc ggcatcctgt tttcgcacaa ccggaccgaa    3780
aacaccttcg acgacggcat cggcaactcg gcacggcttg cccacggcgc cgttttcggg    3840
caatacggca tcgacaggtt ctacatcggc atcagcgcgg gcgcgggttt tagcagcggc    3900
agcctttcag acggcatcgg aggcaaaatc cgccgccgcg tgctgcatta cggcattcag    3960
gcacgatacc gcgccggttt cggcggattc ggcatcgaac gcacatcgg cgcaacgcgc    4020 tatttcgtcc aaaagcgga ttaccgctac gaaaacgtca atatcgccac ccccggcctt    4080
gcattcaacc gctaccgcgc gggcattaag gcagattatt cattcaaacc ggcgcaacac    4140
atttccatca cgccttattt gagcctgtcc tataccgatg ccgcttcggg caaagtccga    4200
acacgcgtca ataccgccgt attggctcag gatttcggca aaacccgcag tgcggaatgg    4260
ggcgtaaacg ccgaaatcaa aggcttcacg ctgtccctcc acgctgccgc cgccaaaggc    4320
ccgcaactgg aagcgcaaca cagcgcgggc atcaaattag gctaccgctg gtaa          4374
```

<210> SEQ ID NO 4
<211> LENGTH: 1457
<212> TYPE: PRT
<213> ORGANISM: Bacteria

<400> SEQUENCE: 4

```
Met Lys Thr Thr Asp Lys Arg Thr Thr Glu Thr His Arg Lys Ala Pro
1               5                  10                  15
Lys Thr Gly Arg Ile Arg Phe Ser Pro Ala Tyr Leu Ala Ile Cys Leu
            20                  25                  30
Ser Phe Gly Ile Leu Pro Gln Ala Trp Ala Gly His Thr Tyr Phe Gly
        35                  40                  45
Ile Asn Tyr Gln Tyr Tyr Arg Asp Phe Ala Glu Asn Lys Gly Lys Phe
    50                  55                  60
Ala Val Gly Ala Lys Asp Ile Glu Val Tyr Asn Lys Lys Gly Glu Leu
65                  70                  75                  80
Val Gly Lys Ser Met Thr Lys Ala Pro Met Ile Asp Phe Ser Val Val
                85                  90                  95
Ser Arg Asn Gly Val Ala Ala Leu Val Gly Asp Gln Tyr Ile Val Ser
            100                 105                 110
Val Ala His Asn Gly Gly Tyr Asn Asn Val Asp Phe Gly Ala Glu Gly
        115                 120                 125
Arg Asn Pro Asp Gln His Arg Phe Thr Tyr Lys Ile Val Lys Arg Asn
    130                 135                 140
Asn Tyr Lys Ala Gly Thr Lys Gly His Pro Tyr Gly Gly Asp Tyr His
145                 150                 155                 160
Met Pro Arg Leu His Lys Phe Val Thr Asp Ala Glu Pro Val Glu Met
                165                 170                 175
Thr Ser Tyr Met Asp Gly Arg Lys Tyr Ile Asp Gln Asn Asn Tyr Pro
            180                 185                 190
Asp Arg Val Arg Ile Gly Ala Gly Arg Gln Tyr Trp Arg Ser Asp Glu
        195                 200                 205
Asp Glu Pro Asn Arg Glu Ser Ser Tyr His Ile Ala Ser Ala Tyr
    210                 215                 220
Ser Trp Leu Val Gly Gly Asn Thr Phe Ala Gln Asn Gly Ser Gly Gly
225                 230                 235                 240
Gly Thr Val Asn Leu Gly Ser Glu Lys Ile Lys His Ser Pro Tyr Gly
                245                 250                 255
Phe Leu Pro Thr Gly Gly Ser Phe Gly Asp Ser Gly Ser Pro Met Phe
            260                 265                 270
Ile Tyr Asp Ala Gln Lys Gln Lys Trp Leu Ile Asn Gly Val Leu Gln
        275                 280                 285
Thr Gly Asn Pro Tyr Ile Gly Lys Ser Asn Gly Phe Gln Leu Val Arg
    290                 295                 300
Lys Asp Trp Phe Tyr Asp Glu Ile Phe Ala Gly Asp Thr His Ser Val
305                 310                 315                 320
Phe Tyr Glu Pro Arg Gln Asn Gly Lys Tyr Ser Phe Asn Asp Asp Asn
                325                 330                 335
Asn Gly Thr Gly Lys Ile Asn Ala Lys His Glu His Asn Ser Leu Pro
            340                 345                 350
Asn Arg Leu Lys Thr Arg Thr Val Gln Leu Phe Asn Val Ser Leu Ser
        355                 360                 365
Glu Thr Ala Arg Glu Pro Val Tyr His Ala Ala Gly Gly Val Asn Ser
    370                 375                 380
Tyr Arg Pro Arg Leu Asn Asn Gly Glu Asn Ile Ser Phe Ile Asp Glu
385                 390                 395                 400
Gly Lys Gly Glu Leu Ile Leu Thr Ser Asn Ile Asn Gln Gly Ala Gly
```

-continued

```
                405                 410                 415
Gly Leu Tyr Phe Gln Gly Asp Phe Thr Val Ser Pro Glu Asn Asn Glu
                420                 425                 430

Thr Trp Gln Gly Ala Gly Val His Ile Ser Glu Asp Ser Thr Val Thr
                435                 440                 445

Trp Lys Val Asn Gly Val Ala Asn Asp Arg Leu Ser Lys Ile Gly Lys
                450                 455                 460

Gly Thr Leu His Val Gln Ala Lys Gly Glu Asn Gln Gly Ser Ile Ser
465                 470                 475                 480

Val Gly Asp Gly Thr Val Ile Leu Asp Gln Gln Ala Asp Asp Lys Gly
                485                 490                 495

Lys Lys Gln Ala Phe Ser Glu Ile Gly Leu Val Ser Gly Arg Gly Thr
                500                 505                 510

Val Gln Leu Asn Ala Asp Asn Gln Phe Asn Pro Asp Lys Leu Tyr Phe
                515                 520                 525

Gly Phe Arg Gly Gly Arg Leu Asp Leu Asn Gly His Ser Leu Ser Phe
                530                 535                 540

His Arg Ile Gln Asn Thr Asp Glu Gly Ala Met Ile Val Asn His Asn
545                 550                 555                 560

Gln Asp Lys Glu Ser Thr Val Thr Ile Thr Gly Asn Lys Asp Ile Ala
                565                 570                 575

Thr Thr Gly Asn Asn Asn Ser Leu Asp Ser Lys Lys Glu Ile Ala Tyr
                580                 585                 590

Asn Gly Trp Phe Gly Glu Lys Asp Thr Thr Lys Thr Asn Gly Arg Leu
                595                 600                 605

Asn Leu Val Tyr Gln Pro Ala Ala Glu Asp Arg Thr Leu Leu Leu Ser
                610                 615                 620

Gly Gly Thr Asn Leu Asn Gly Asn Ile Thr Gln Thr Asn Gly Lys Leu
625                 630                 635                 640

Phe Phe Ser Gly Arg Pro Thr Pro His Ala Tyr Asn His Leu Asn Asp
                645                 650                 655

His Trp Ser Gln Lys Glu Gly Ile Pro Arg Gly Glu Ile Val Trp Asp
                660                 665                 670

Asn Asp Trp Ile Asn Arg Thr Phe Lys Ala Glu Asn Phe Gln Ile Lys
                675                 680                 685

Gly Gly Gln Ala Val Val Ser Arg Asn Val Ala Lys Val Lys Gly Asp
                690                 695                 700

Trp His Leu Ser Asn His Ala Gln Ala Val Phe Gly Val Ala Pro His
705                 710                 715                 720

Gln Ser His Thr Ile Cys Thr Arg Ser Asp Trp Thr Gly Leu Thr Asn
                725                 730                 735

Cys Val Glu Lys Thr Ile Thr Asp Asp Lys Val Ile Ala Ser Leu Thr
                740                 745                 750

Lys Thr Asp Ile Ser Gly Asn Val Asp Leu Ala Asp His Ala His Leu
                755                 760                 765

Asn Leu Thr Gly Leu Ala Thr Leu Asn Gly Asn Leu Ser Ala Asn Gly
                770                 775                 780

Asp Thr Arg Tyr Thr Val Ser His Asn Ala Thr Gln Asn Gly Asn Leu
785                 790                 795                 800

Ser Leu Val Gly Asn Ala Gln Ala Thr Phe Asn Gln Ala Thr Leu Asn
                805                 810                 815

Gly Asn Thr Ser Ala Ser Gly Asn Ala Ser Phe Asn Leu Ser Asp His
                820                 825                 830
```

```
Ala Val Gln Asn Gly Ser Leu Thr Leu Ser Gly Asn Ala Lys Ala Asn
            835                 840                 845

Val Ser His Ser Ala Leu Asn Gly Asn Val Ser Leu Ala Asp Lys Ala
            850                 855                 860

Val Phe His Phe Glu Ser Ser Arg Phe Thr Gly Gln Ile Ser Gly Gly
865                 870                 875                 880

Lys Asp Thr Ala Leu His Leu Lys Asp Ser Glu Trp Thr Leu Pro Ser
                885                 890                 895

Gly Thr Glu Leu Gly Asn Leu Asn Leu Asp Asn Ala Thr Ile Thr Leu
            900                 905                 910

Asn Ser Ala Tyr Arg His Asp Ala Ala Gly Ala Gln Thr Gly Ser Ala
            915                 920                 925

Thr Asp Ala Pro Arg Arg Ser Arg Arg Ser Arg Arg Ser Leu Leu
            930                 935                 940

Ser Val Thr Pro Pro Thr Ser Val Glu Ser Arg Phe Asn Thr Leu Thr
945                 950                 955                 960

Val Asn Gly Lys Leu Asn Gly Gln Gly Thr Phe Arg Phe Met Ser Glu
                965                 970                 975

Leu Phe Gly Tyr Arg Ser Asp Lys Leu Lys Leu Ala Glu Ser Ser Glu
            980                 985                 990

Gly Thr Tyr Thr Leu Ala Val Asn Asn Thr Gly Asn Glu Pro Ala Ser
            995                 1000                1005

Leu Glu Gln Leu Thr Val Val Glu Gly Lys Asp Asn Lys Pro Leu Ser
            1010                1015                1020

Glu Asn Phe Asn Phe Thr Leu Gln Asn Glu His Val Asp Ala Gly Ala
1025                1030                1035                1040

Trp Arg Tyr Gln Leu Ile Arg Lys Asp Gly Glu Phe Arg Leu His Asn
                1045                1050                1055

Pro Val Lys Glu Gln Glu Leu Ser Asp Lys Leu Gly Lys Ala Glu Ala
            1060                1065                1070

Lys Lys Gln Ala Glu Lys Asp Asn Ala Gln Ser Leu Asp Ala Leu Ile
            1075                1080                1085

Ala Ala Gly Arg Asp Ala Val Glu Lys Thr Glu Ser Val Ala Glu Pro
            1090                1095                1100

Ala Arg Gln Ala Gly Gly Glu Asn Val Gly Ile Met Gln Ala Glu Glu
1105                1110                1115                1120

Glu Lys Lys Arg Val Gln Ala Asp Lys Asp Thr Ala Leu Ala Lys Gln
                1125                1130                1135

Arg Glu Ala Glu Thr Arg Pro Ala Thr Thr Ala Phe Pro Arg Ala Arg
            1140                1145                1150

Arg Ala Arg Arg Asp Leu Pro Gln Leu Gln Pro Gln Pro Gln
            1155                1160                1165

Pro Gln Arg Asp Leu Ile Ser Arg Tyr Ala Asn Ser Gly Leu Ser Glu
            1170                1175                1180

Phe Ser Ala Thr Leu Asn Ser Val Phe Ala Val Gln Asp Glu Leu Asp
1185                1190                1195                1200

Arg Val Phe Ala Glu Glu Arg Arg Asn Ala Val Trp Thr Ser Gly Ile
                1205                1210                1215

Arg Asp Thr Lys His Tyr Arg Ser Gln Asp Phe Arg Ala Tyr Arg Gln
            1220                1225                1230

Gln Thr Asp Leu Arg Gln Ile Gly Met Gln Lys Asn Leu Gly Ser Gly
            1235                1240                1245
```

-continued

```
Arg Val Gly Ile Leu Phe Ser His Asn Arg Thr Glu Asn Thr Phe Asp
        1250                1255                1260
Asp Gly Ile Gly Asn Ser Ala Arg Leu Ala His Gly Ala Val Phe Gly
1265                1270                1275                1280
Gln Tyr Gly Ile Asp Arg Phe Tyr Ile Gly Ile Ser Ala Gly Ala Gly
                1285                1290                1295
Phe Ser Ser Gly Ser Leu Ser Asp Gly Ile Gly Lys Ile Arg Arg
        1300                1305                1310
Arg Val Leu His Tyr Gly Ile Gln Ala Arg Tyr Arg Ala Gly Phe Gly
            1315                1320                1325
Gly Phe Gly Ile Glu Pro His Ile Gly Ala Thr Arg Tyr Phe Val Gln
    1330                1335                1340
Lys Ala Asp Tyr Arg Tyr Glu Asn Val Asn Ile Ala Thr Pro Gly Leu
1345                1350                1355                1360
Ala Phe Asn Arg Tyr Arg Ala Gly Ile Lys Ala Asp Tyr Ser Phe Lys
                1365                1370                1375
Pro Ala Gln His Ile Ser Ile Thr Pro Tyr Leu Ser Leu Ser Tyr Thr
            1380                1385                1390
Asp Ala Ala Ser Gly Lys Val Arg Thr Arg Val Asn Thr Ala Val Leu
        1395                1400                1405
Ala Gln Asp Phe Gly Lys Thr Arg Ser Ala Glu Trp Gly Val Asn Ala
    1410                1415                1420
Glu Ile Lys Gly Phe Thr Leu Ser Leu His Ala Ala Ala Lys Gly
1425                1430                1435                1440
Pro Gln Leu Glu Ala Gln His Ser Ala Gly Ile Lys Leu Gly Tyr Arg
                1445                1450                1455
Trp

<210> SEQ ID NO 5
<211> LENGTH: 34
<212> TYPE: DNA
<213> ORGANISM: Artificial Sequence
<220> FEATURE:
<223> OTHER INFORMATION: Primer

<400> SEQUENCE: 5 ggggctagc aaaacaaccg acaaacggac aacc                                  34

<210> SEQ ID NO 6
<211> LENGTH: 40
<212> TYPE: DNA
<213> ORGANISM: Artificial Sequence
<220> FEATURE:
<223> OTHER INFORMATION: Primer

<400> SEQUENCE: 6
ggggaagctt ccagcggtag cggtagccta atttgatgcc                           40
```